(12) United States Patent
Oldknow et al.

(10) Patent No.: US 12,357,885 B2
(45) Date of Patent: Jul. 15, 2025

(54) IRON-TYPE GOLF CLUBS AND GOLF CLUB HEADS

(71) Applicant: KARSTEN MANUFACTURING CORPORATION, Phoenix, AZ (US)

(72) Inventors: Andrew G. V. Oldknow, Beaverton, OR (US); Nathaniel J. Radcliffe, Trophy Club, TX (US)

(73) Assignee: Karsten Manufacturing Corporation, Phoenix, AZ (US)

( * ) Notice: Subject to any disclaimer, the term of this patent is extended or adjusted under 35 U.S.C. 154(b) by 0 days.

(21) Appl. No.: 18/314,740

(22) Filed: May 9, 2023

(65) Prior Publication Data

US 2023/0301262 A1  Sep. 28, 2023

Related U.S. Application Data

(63) Continuation of application No. 17/451,469, filed on Oct. 19, 2021, now Pat. No. 11,642,578, which is a
(Continued)

(51) Int. Cl.
*A63B 53/04* (2015.01)
*A01H 5/10* (2018.01)
(Continued)

(52) U.S. Cl.
CPC ............ *A63B 53/047* (2013.01); *A01H 5/10* (2013.01); *A01H 5/12* (2013.01); *A01H 6/1472* (2018.05);
(Continued)

(58) Field of Classification Search
CPC .............. A63B 53/047; A63B 53/0475; A63B 2053/0479; A63B 2053/0483
See application file for complete search history.

(56) References Cited

U.S. PATENT DOCUMENTS

D92,266 S      5/1934  Nicoll et al.
2,007,377 A  *  7/1935  Link ..................... A63B 53/047
                                                         473/350
(Continued)

FOREIGN PATENT DOCUMENTS

EP   2889061 A1 *  7/2015  ............... A01H 5/10
GB   2251556         7/1992
(Continued)

OTHER PUBLICATIONS

International Search Report for PCT Application No. PCT/US1999/002000, 2 pages, May 17, 1999.

*Primary Examiner* — Alvin A Hunter

(57) ABSTRACT

In general, aspects of this invention relate to blade-type iron golf clubs or golf club heads. The blade-type golf club head may comprise a body forged of a metal material. The body may include a hosel, a top surface, a sole, a heel, a toe, a ball striking surface, and a rear surface opposite the ball striking surface. The rear surface may have an upper blade portion and a lower muscle portion with the upper blade portion separated from the lower muscle portion by a blade interface. The lower muscle portion may have a muscle portion surface are that includes a heel muscle surface area measured from the ball striking centerline to the heel and a toe muscle surface area measured from the ball striking centerline to the toe. The toe muscle surface area may make up at least 60% of the muscle portion surface area. The mass distribution of the lower muscle portion moves the center of gravity of the club head closer to the face center location.

20 Claims, 16 Drawing Sheets

Related U.S. Application Data continuation of application No. 16/882,523, filed on May 24, 2020, now Pat. No. 11,148,019, which is a continuation of application No. 16/125,108, filed on Sep. 7, 2018, now Pat. No. 10,661,130, which is a continuation of application No. 15/485,687, filed on Apr. 12, 2017, now Pat. No. 10,092,800, which is a continuation of application No. 15/077,418, filed on Mar. 22, 2016, now Pat. No. 9,623,300, which is a continuation of application No. 14/534,915, filed on Nov. 6, 2014, now Pat. No. 9,427,633, which is a continuation of application No. 14/284,968, filed on May 22, 2014, now Pat. No. 9,295,887.

(60) Provisional application No. 61/922,756, filed on Dec. 31, 2013.

(51) Int. Cl.
- *A01H 5/12* (2018.01)
- *A01H 6/14* (2018.01)
- *A63B 60/02* (2015.01)

(52) U.S. Cl.
CPC .......... *A63B 60/02* (2015.10); *A63B 53/0408* (2020.08); *A63B 53/0458* (2020.08); *A63B 2053/0491* (2013.01)

(56) References Cited

U.S. PATENT DOCUMENTS

| | | | |
|---|---|---|---|
| D115,217 S | 6/1939 | Newsome | |
| D125,455 S | 2/1941 | Newsome | |
| D164,597 S | 9/1951 | Penna | |
| D179,092 S | 10/1956 | Favlis | |
| 3,655,188 A | 4/1972 | Solheim | |
| 3,979,122 A | 9/1976 | Belmont | |
| 4,200,286 A * | 4/1980 | Bennett | A63B 53/00 473/289 |
| 4,345,763 A | 8/1982 | Swanson | |
| 4,420,156 A | 12/1983 | Campau | |
| 4,787,636 A * | 11/1988 | Honma | A63B 53/04 473/349 |
| 4,802,672 A | 2/1989 | Long | |
| 4,811,950 A | 3/1989 | Kobayashi | |
| 4,852,880 A | 8/1989 | Kobayashi | |
| 5,295,686 A | 3/1994 | Lundberg | |
| 5,320,347 A | 6/1994 | Parente | |
| 5,375,840 A | 12/1994 | Hirsch | |
| 5,649,872 A * | 7/1997 | Antonious | A63B 60/00 D21/748 |
| 5,800,282 A | 9/1998 | Hutin | |
| D408,485 S | 4/1999 | Takahashi | |
| 6,093,113 A | 7/2000 | Mertens | |
| 6,482,104 B1 | 11/2002 | Gilbert | |
| D469,832 S | 2/2003 | Bode | |
| 6,530,846 B1 | 3/2003 | Mase | |
| D473,606 S | 4/2003 | Mickelson | |
| 6,551,200 B1 * | 4/2003 | Golden | A63B 53/047 473/349 |
| 6,592,469 B2 | 7/2003 | Gilbert | |
| 6,620,055 B2 * | 9/2003 | Saso | A63B 60/00 473/324 |
| 6,849,005 B2 * | 2/2005 | Rife | A63B 60/02 473/332 |
| 6,863,625 B2 * | 3/2005 | Reyes | A63B 53/0466 473/330 |
| 6,935,967 B2 * | 8/2005 | Mahaffey | A63B 60/00 473/291 |
| 7,125,343 B2 * | 10/2006 | Imamoto | A63B 53/04 473/347 |
| 7,186,187 B2 * | 3/2007 | Gilbert | A63B 53/047 473/290 |
| 7,303,487 B2 | 12/2007 | Kumamoto | |
| 7,316,623 B2 * | 1/2008 | Imamoto | A63B 53/047 473/332 |
| 7,380,325 B2 * | 6/2008 | Takeda | A63B 53/047 473/324 |
| 7,390,270 B2 | 6/2008 | Roberts | |
| D603,918 S | 11/2009 | Simon | |
| 7,878,920 B2 * | 2/2011 | Clausen | A63B 53/047 473/291 |
| 7,976,403 B2 * | 7/2011 | Gilbert | A63B 53/04 473/309 |
| D673,629 S | 1/2013 | Breier | |
| 8,419,568 B2 | 4/2013 | Roberts | |
| 8,480,507 B2 * | 7/2013 | Finn | A63B 53/047 473/291 |
| 8,491,414 B2 * | 7/2013 | Dill | A63B 60/02 473/335 |
| 8,500,573 B2 | 8/2013 | Rick | |
| 8,568,249 B2 * | 10/2013 | Gilbert | A63B 53/04 473/349 |
| 8,579,729 B2 | 11/2013 | Nelson | |
| D696,366 S | 12/2013 | Milo | |
| 8,740,722 B2 * | 6/2014 | Sato | A63B 53/047 473/349 |
| 8,753,219 B2 | 6/2014 | Gilbert | |
| 8,795,102 B2 | 8/2014 | Knight | |
| 8,876,624 B2 | 11/2014 | Ban | |
| 8,926,451 B2 * | 1/2015 | Deshmukh | B21K 17/00 473/349 |
| 8,961,336 B1 * | 2/2015 | Parsons | A63B 53/0475 473/335 |
| 9,295,887 B2 * | 3/2016 | Radcliffe | A63B 53/047 |
| 9,427,633 B2 * | 8/2016 | Oldknow | A63B 53/047 |
| 9,623,300 B2 * | 4/2017 | Oldknow | A63B 53/047 |
| 10,086,238 B1 * | 10/2018 | Roach | A63B 60/42 |
| 10,092,800 B2 * | 10/2018 | Oldknow | A63B 53/047 |
| 10,661,130 B2 * | 5/2020 | Oldknow | A63B 53/047 |
| 10,758,792 B2 * | 9/2020 | Shimahara | A63B 53/047 |
| 11,642,578 B2 * | 5/2023 | Oldknow | A01H 6/1472 473/324 |
| 2004/0254027 A1 * | 12/2004 | Mahaffey | A63B 53/047 473/287 |
| 2005/0014573 A1 * | 1/2005 | Lee | A63B 53/0475 473/335 |
| 2009/0176596 A1 | 7/2009 | Kobayashi | |
| 2012/0157223 A1 * | 6/2012 | Finn | A63B 53/0466 473/291 |
| 2015/0126301 A1 * | 5/2015 | Taylor | A63B 53/047 473/324 |
| 2015/0182815 A1 | 7/2015 | Boggs | |
| 2015/0182816 A1 * | 7/2015 | Radcliffe | A63B 53/047 473/324 |
| 2015/0182817 A1 * | 7/2015 | Oldknow | A63B 53/047 473/324 |
| 2016/0199705 A1 * | 7/2016 | Oldknow | A63B 53/047 473/349 |
| 2017/0216685 A1 * | 8/2017 | Oldknow | A63B 53/047 |
| 2018/0093145 A1 * | 4/2018 | Ripp | A63B 60/50 |
| 2019/0168084 A1 * | 6/2019 | Seagram | C23C 24/04 |
| 2020/0298077 A1 * | 9/2020 | Clarke | A63B 60/50 |
| 2021/0402265 A1 * | 12/2021 | Clarke | A63B 60/02 |
| 2022/0032131 A1 * | 2/2022 | Oldknow | A01H 6/1472 |
| 2023/0301262 A1 * | 9/2023 | Oldknow | A63B 53/047 |
| 2024/0042287 A1 * | 2/2024 | Ripp | A63B 53/047 |

FOREIGN PATENT DOCUMENTS

| | | | | |
|---|---|---|---|---|
| GB | 2251556 A | * | 7/1992 | ........... A63B 53/04 |
| JP | 01113082 A | * | 5/1989 | |
| JP | 02063483 A | * | 3/1990 | |
| JP | H0263483 | | 3/1990 | |
| JP | 03023877 A | * | 1/1991 | |
| JP | H0323877 | | 1/1991 | |
| JP | 04227285 A | * | 8/1992 | |
| JP | H04227285 | | 8/1992 | |
| JP | H04241882 | | 8/1992 | |
| JP | 07299164 A | * | 11/1995 | ........... A63B 53/047 |
| JP | H07299164 | | 11/1995 | |

(56) References Cited

FOREIGN PATENT DOCUMENTS

| JP | 09271544 A | * | 10/1997 | | |
| JP | H09271544 | | 10/1997 | | |
| JP | 09322952 A | * | 12/1997 | | |
| JP | H09322952 | | 12/1997 | | |
| JP | 2005185751 | | 7/2005 | | |
| JP | 2005185751 A | * | 7/2005 | | |
| JP | 2006167033 | | 6/2006 | | |
| JP | 2006167033 A | * | 6/2006 | | |
| JP | 2007209540 | | 8/2007 | | |
| JP | 2007209540 A | * | 8/2007 | | |
| JP | 2007222231 | | 9/2007 | | |
| JP | 2007222231 A | * | 9/2007 | | |
| JP | 2009240587 | | 10/2009 | | |
| JP | 2009240587 A | * | 10/2009 | | |
| JP | 2012213607 | | 11/2012 | | |
| JP | 2012213607 A | * | 11/2012 | | |
| JP | 2013000161 | | 1/2013 | | |
| JP | 2013000161 A | * | 1/2013 | | |
| JP | 2013144102 A | * | 7/2013 | ........... | A63B 53/047 |
| WO | WO-9938576 A1 | * | 8/1999 | ............. | A63B 53/04 |

* cited by examiner

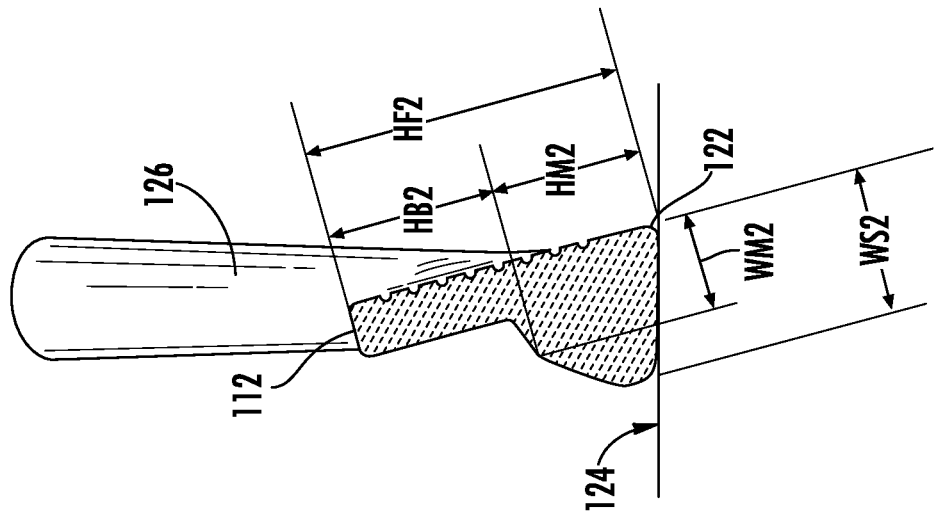
FIG. 16C (CROSS-SECTION L2)
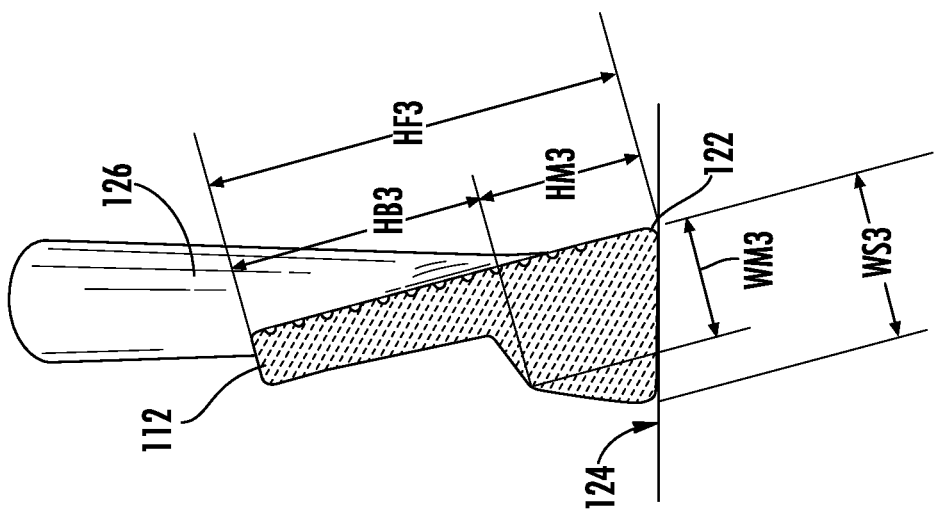
FIG. 16B (CROSS-SECTION L3)
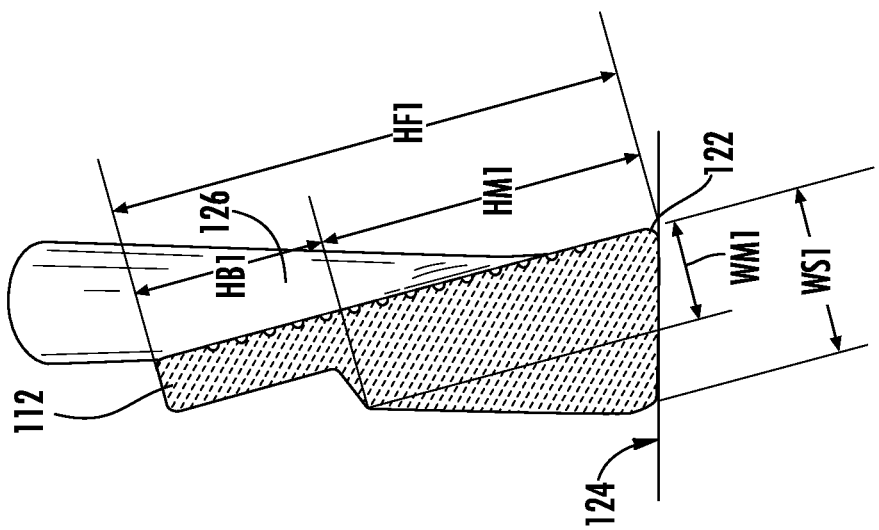
FIG. 16A (CROSS-SECTION L1)

IRON-TYPE GOLF CLUBS AND GOLF CLUB HEADS

This is a continuation of U.S. patent application Ser. No. 17/451,469, filed on Oct. 19, 2021, now U.S. Pat. No. 11,642,578, which is a continuation of U.S. patent application Ser. No. 16/882,523, filed on May 24, 2020, now U.S. Pat. No. 11,148,019, which is a continuation of U.S. patent application Ser. No. 16/125,108, filed Sep. 7, 2018, now U.S. Pat. No. 10,661,130, which is a continuation of U.S. patent application Ser. No. 15/485,687, filed Apr. 12, 2017, now U.S. Pat. No. 10,092,800, which is a continuation of U.S. patent application Ser. No. 15/077,418, filed Mar. 22, 2016, now U.S. Pat. No. 9,623,300, which is a continuation of U.S. patent application Ser. No. 14/534,915, filed Nov. 6, 2014, now U.S. Pat. No. 9,427,633, which is a continuation of U.S. patent application Ser. No. 14/284,968, filed May 22, 2014, now U.S. Pat. No. 9,295,887, which claims the benefit to U.S. Provisional Application No. 61/922,756, filed Dec. 31, 2013, which are incorporated herein by reference in their entirety.

FIELD OF THE INVENTION

This invention relates generally to golf clubs and golf club heads, and more particularly muscle-back or blade iron golf clubs and golf club heads.

BACKGROUND

Golf clubs are well known in the art for use in the game of golf. Iron type golf clubs generally either have a cavity back configuration or a muscle-back or blade-type configuration. Amateur golfers generally prefer cavity back perimeter-weighted clubs because they produce better shots when not struck near the center of the face. Blade type irons are generally preferred by professional golfers and golfers of higher skill levels because they provide better feel when a golf ball is struck in the center of the face and more feedback when not struck on the center of the face. Blade irons also permit golfers to more readily shape shots by adding different types of spin to the ball, whereas cavity-backs minimize the ability to shape shots.

Cavity-back iron type club heads, also known as perimeter weighted irons, are known to have a concentration of mass about the periphery of a rear surface of the club head. This concentration of mass is in a raised, rib-like, perimeter weighting element that substantially surrounds a rear cavity, which comprises a major portion of the rear surface of the club head. In addition to locating a substantial amount of mass away from the center of the club head behind the club face, the rib-like perimeter weighting element acts as a structural stiffener, which compensates for reduction in face thickness in the cavity region.

Muscle-back or blade irons are characterized by a thick lower portion known as the "muscle", which extends along the entire length of the head. A thin upper portion extends upwardly from the muscle and behind the face of the club, and is commonly referred to as the blade portion. The blade portion may not have reinforcement ribs or perimeter weighting, and may have substantial mass concentrated in the muscle of the club extending along the sole and the entire length of the club head. Typically, a muscle-back club head is smaller than a cavity-back head.

Generally, muscle-back or blade irons have a center of gravity located away from the face center location, typically on the heel and sole side of the face center location. It is generally understood that the closer the center of gravity of the club head is to the face center, the better the club will feel and perform at impact when hitting the golf ball on the face center location.

The present invention seeks to overcome these limitations and other drawbacks of known muscle-back or blade iron golf clubs and golf club heads.

SUMMARY

The following presents a general summary of aspects of the invention in order to provide a basic understanding of the invention and various features of it. This summary is not intended to limit the scope of the invention in any way, but it simply provides a general overview and context for the more detailed description that follows.

According to aspects of this invention, an iron-type golf club head may comprise a top surface, a sole, a heel, and a toe. The iron-type golf club head may be a blade-type iron golf club head further defined with the top surface having a width of no greater than 8 mm and the sole having a width of no greater than 16 mm. The iron-type golf club head may further comprise a ball striking surface configured for striking a ball. The iron-type golf club head may include a leading edge defined as a forward most surface connecting the sole and the ball striking face. The iron-type golf club head may include a leading edge defined as a forward most surface connecting the sole and the ball striking face. The ball striking surface may have a ball striking area that defines a heel-side boundary line, a toe-side boundary line, and a ball striking centerline located equidistant between the heel-side boundary line and the toe-side boundary line. The iron-type golf club head may further comprise a rear surface opposite the ball striking surface. The rear surface may have a separate upper blade portion and a lower muscle portion. The upper blade portion may be separated from the lower muscle portion by a blade interface. The upper blade portion and the lower muscle portion may extend across the rear surface from the heel to the toe. The upper blade portion may extend from the top surface to the blade interface. The lower muscle portion may extend from the blade interface to the sole. Additionally, the upper blade portion may have a generally uniform thickness from the heel to the toe which is between approximately 6 mm and 8 mm. The lower muscle portion may have a thickness greater than the upper blade portion thickness. The lower muscle portion thickness may be between approximately 8 mm and 16 mm. The lower muscle portion may have a height measured from the blade interface to the leading edge. Additionally, an average height of the lower muscle portion from the ball striking centerline to the toe-side boundary line may be at least 50% greater than an average height of the lower muscle portion from the heel-side boundary line to the ball striking centerline.

Additionally, another aspect of this invention may relate to the blade interface. The blade interface may be a smooth arcuate surface that forms a transition area between the upper blade portion and the lower muscle portion. Additionally, the blade interface may include a first blade interface and a second blade interface intersecting the first blade interface at a convergence point. The first blade interface may be generally parallel to the leading edge extending from the heel to the convergence point. The second blade interface may extend upward from the convergence point to the toe. The convergence point may be located approximately along the ball striking centerline. The second blade interface may extend upward at an interface angle between approximately 105 degrees and 155 degrees.

Additionally, another aspect of this invention may relate to a blade-type iron golf club in accordance with examples of this invention. The blade-type iron golf club may comprise a blade-type golf club head and a shaft attached to the blade-type golf club head. The blade-type golf club head may comprise a body forged of a metal material. The body may include a hosel, a top surface, a sole, a heel, and a toe. The blade-type golf club head may further comprise a ball striking surface configured for striking a ball. The iron-type golf club head may include a leading edge defined as a forward most surface connecting the sole and the ball striking face. The ball striking surface may define a heel-side boundary line, a toe-side boundary line, and a ball striking centerline located equidistant between the heel-side boundary line and the toe-side boundary line. The club head may further comprise a rear surface opposite the ball striking surface. The rear surface may have an upper blade portion and a lower muscle portion with the upper blade portion separated from the lower muscle portion by a blade interface. The upper blade portion and the lower muscle portion may extend across the rear surface from the heel to the toe. The upper blade portion may extend from the top surface to the blade interface. The lower muscle portion may extend from the blade interface to the sole. The upper blade portion may have a generally uniform thickness from the heel to the toe. The lower muscle portion may have a thickness greater than the upper blade portion thickness. The lower muscle portion may have a height measured from the blade interface to the leading edge. The height at the toe-side boundary line may be greater than approximately 26 mm and the height at the heel-side boundary line may be less than approximately 14 mm. In another club head embodiment, the height at the toe-side boundary line may be greater than approximately 30 mm and the height at the heel-side boundary line may be less than approximately 16 mm. In yet another club head embodiment, the height at the toe-side boundary line may be greater than approximately 36 mm and the height at the heel-side boundary line may be less than approximately 18 mm.

Additional aspects of this invention relate to a blade-type iron golf club head. The blade-type golf club head may comprise a ball striking surface and a rear surface opposite the ball striking surface. The ball striking surface may be configured for striking a ball. The ball striking surface may have a ball striking area that defines a heel-side boundary line, a toe-side boundary line, and a ball striking centerline located equidistant between the heel-side boundary line and the toe-side boundary line. The rear surface may have a separate upper blade portion and a lower muscle portion. The upper blade portion may be separated from the lower muscle portion by a blade interface. The upper blade portion and the lower muscle portion may laterally extend across the rear surface. The upper blade portion may extend upward from the blade interface. The lower muscle portion may extend downward from the blade interface. The upper blade portion may have a generally uniform thickness of between approximately 6 mm and 8 mm. The lower muscle portion may have a thickness greater than the upper blade portion thickness. The lower muscle portion thickness may be between approximately 8 mm and 16 mm. The lower muscle portion may have an average height from the ball striking centerline to the toe-side boundary line that is at least 50% greater than an average height of the lower muscle portion from the heel-side boundary line to the ball striking centerline. Additionally, the blade-type golf club head may further include a toe surface area of the lower muscle portion located between the toe-side boundary line to the ball striking centerline that is 2 time greater than a heel surface area of the lower muscle portion located between the heel-side boundary line to the ball striking centerline.

BRIEF DESCRIPTION OF THE DRAWINGS

A more complete understanding of the present invention and certain advantages thereof may be acquired by referring to the following detailed description in consideration with the accompanying drawings, in which:

FIGS. 16A through 16C illustrate cross-sectional views along lines L1, L3 and L2 respectively of the golf club head illustrated in FIG. 8 according to this invention;

The reader is advised that the attached drawings are not necessarily drawn to scale.

DETAILED DESCRIPTION

In the following description of various example structures in accordance with the invention, reference is made to the accompanying drawings, which form a part hereof, and in which are shown by way of illustration various example adjustment members, golf club heads, and golf club structures in accordance with the invention. Additionally, it is to be understood that other specific arrangements of parts and structures may be utilized, and structural and functional modifications may be made without departing from the scope of the present invention. Also, while the terms "top," "bottom," "front," "back," "rear," "side," "underside," "overhead," and the like may be used in this specification to describe various example features and elements of the invention, these terms are used herein as a matter of convenience, e.g., based on the example orientations shown in the figures and/or the orientations in typical use. Nothing in this specification should be construed as requiring a specific three dimensional or spatial orientation of structures in order to fall within the scope of this invention.

Figure 1:
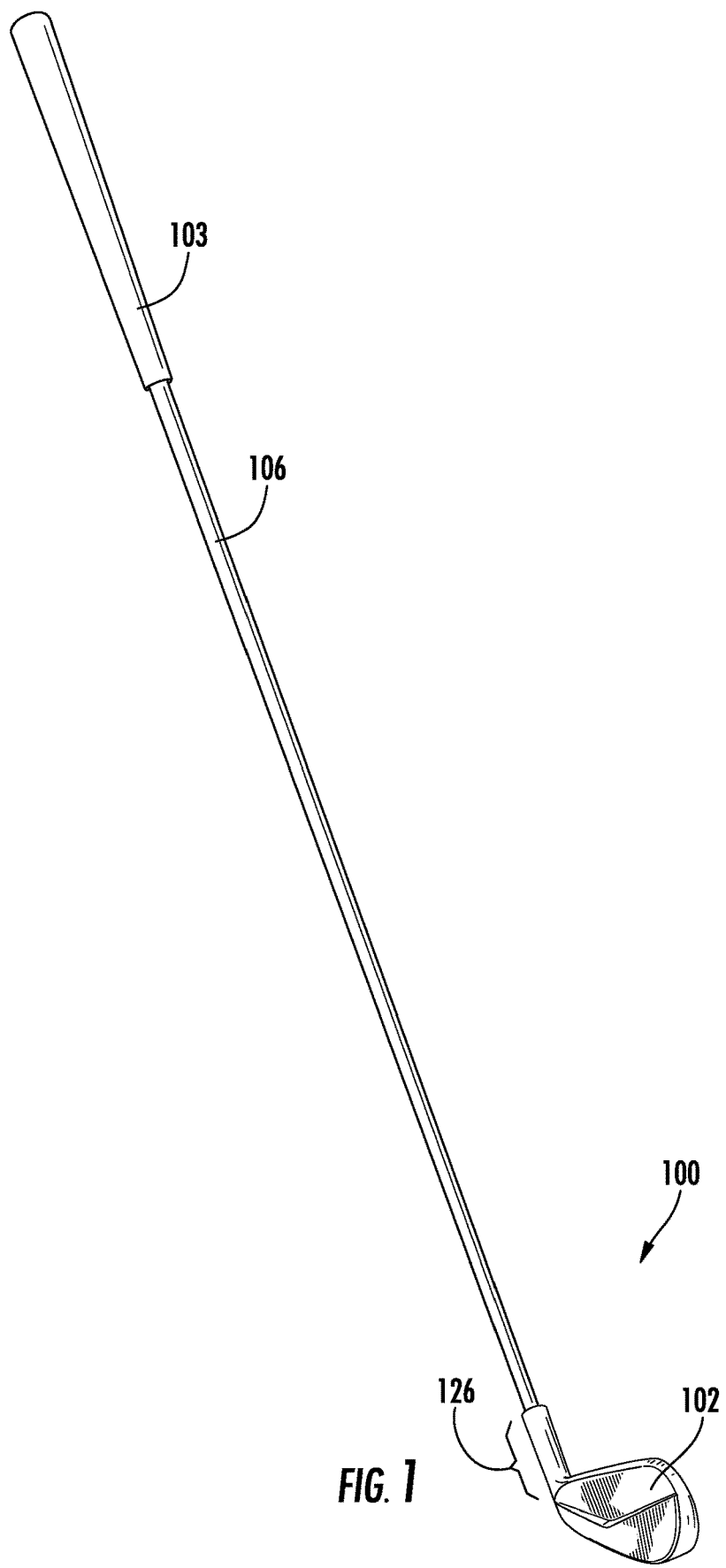
FIG. 1 generally illustrates a perspective view of an example golf club according to this invention.
Figure 2A:
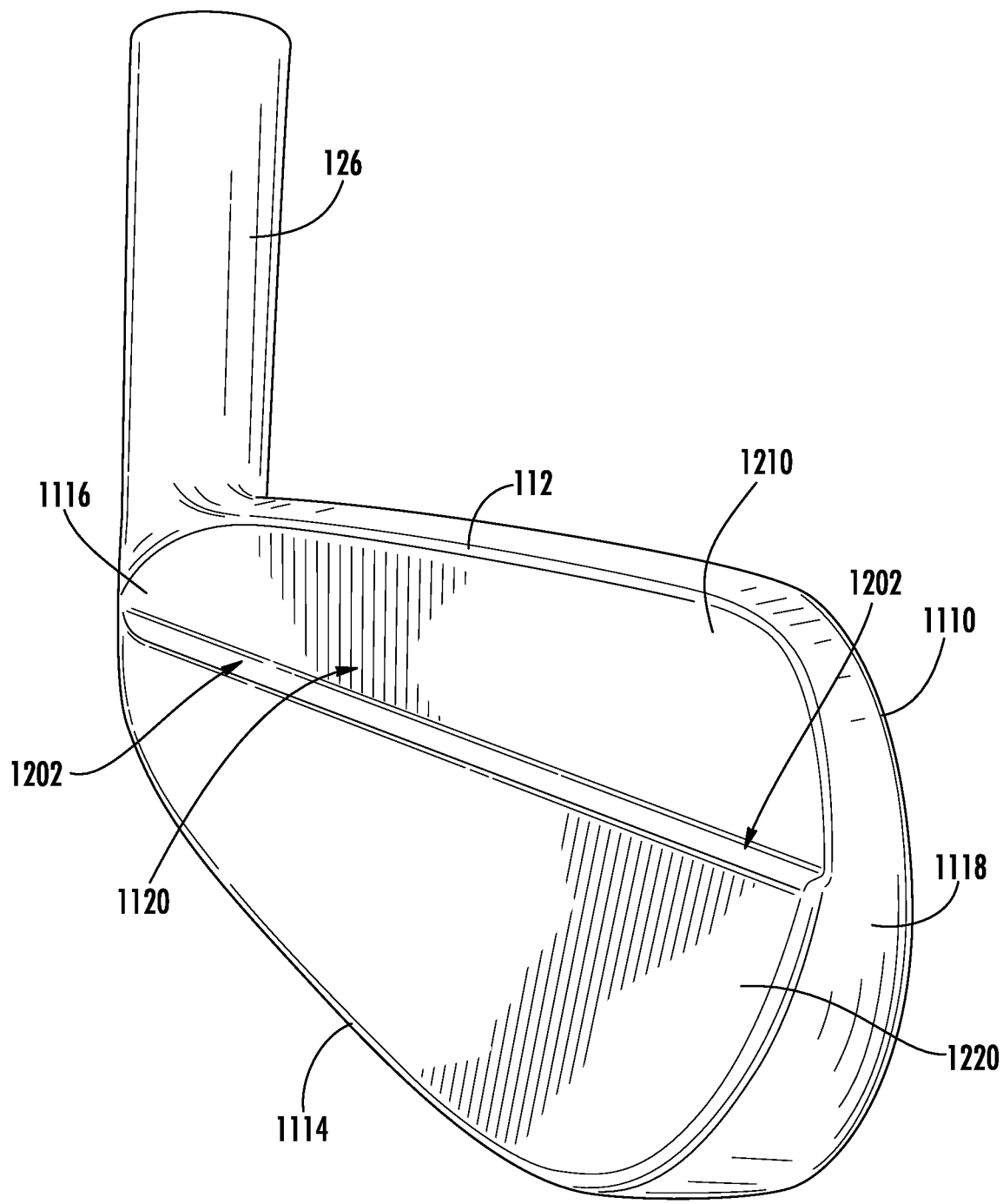
FIG. 2A generally illustrates a perspective rear view of a prior art golf club head.
Figure 2B:
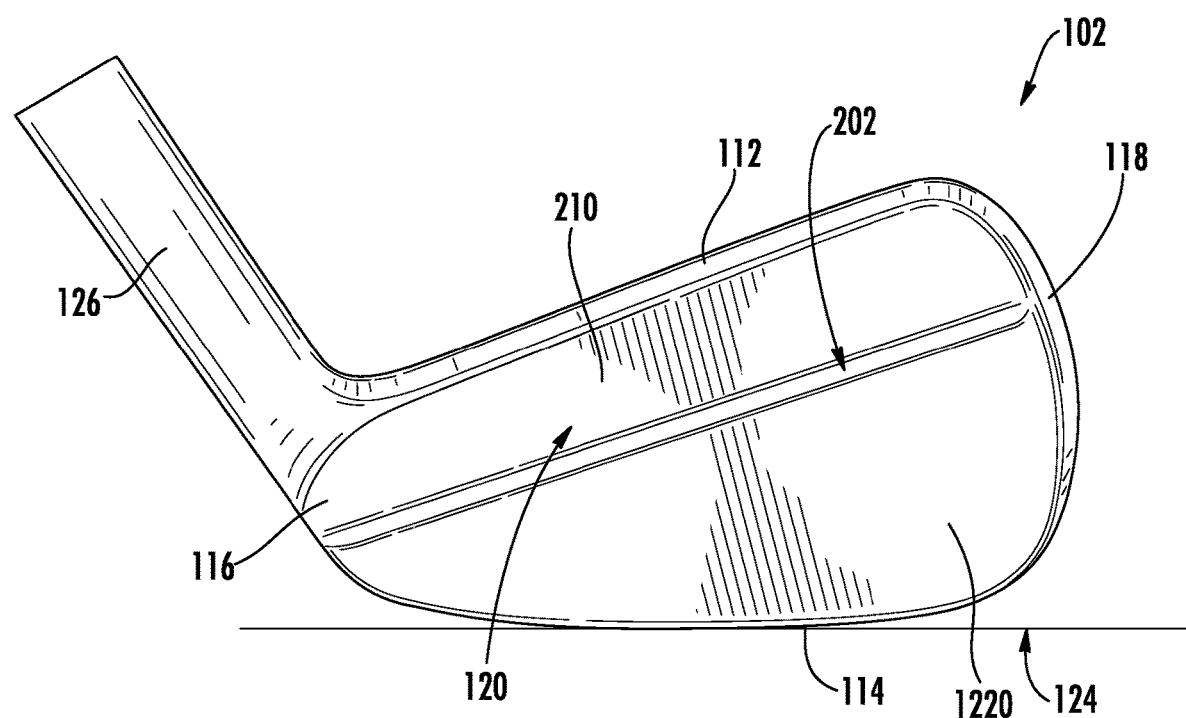
FIG. 2B generally illustrates a rear view of the prior art golf club head of FIG. 2A.

A. General Description of Muscle-Back or Blade-Type Iron Clubs and Club Heads In general, aspects of this invention relate to a set of golf clubs, golf clubs, or golf club heads with a blade-type golf club head. FIG. 1 illustrates an example blade-type golf club head in accordance with aspects of this invention. A blade-type golf club head does not contain any cavities or depressions in the rear surface as distinguished from perimeter-weighted clubs which contain one or more rear cavities. FIGS. 2A and 2B illustrate a prior art golf club head, shown having a traditional muscle-back or blade-type iron configuration. The iron club head 1102 in FIGS. 2A and 2B includes a face or striking face 1110, a top surface 1112, a sole 1114, a heel 1116, a toe 1118, and a rear surface 1120 as was described above. The rear surface 1120 comprises a substantially flat area, which defines a blade portion 1210 of the club head, and a contoured area which defines a muscle portion 1220 of the club head 1102. The blade portion 1210 generally occupies the entire upper portion of the club head 1102, and has a substantially constant thickness that may be less than, for example, approximately 6 mm. The muscle portion 1220 generally constitutes a lower portion of the club head 1102, and has a varying thickness that is everywhere greater than that of blade portion 1210.

The muscle portion 1220 may be generally separated from the upper blade portion 1210 by a blade interface 1202, represented by a phantom line. The blade interface 1202 may be a smooth, arcuate surface forming the transition area between the upper blade portion 1210 and the muscle portion 1220. If there is no distinct boundary separating the muscle portion 1220 and the upper blade portion 1210, the transition between the muscle portion 1220 and the upper blade portion 1210 may occur via a gradual surface curvature. As illustrated in FIGS. 2A and 2B, the blade interface 1202 is a straight line extending across the rear surface 1120 of the club head 1102 from the heel 1116 to the toe 1118.

Additionally, other features and characteristics may be identified with a blade-type or muscle-back iron club head. The blade-type or muscle-back iron club head may be formed of forged metal such as carbon steel in order to increase the feel provided to the golfer. Additionally, the sole width of a blade-type or muscle-back iron club head may be generally thin and constant along the length of the sole. For example, the sole width for blade-type or muscle-back iron club heads may be approximately 10 mm to 19 mm in width. Additionally, the top surface width or blade width (also known as top-line width) may be generally constant along the length of the top surface. For example, the top surface width for blade-type or muscle-back iron club heads may be approximately 3.2 mm to 6.4 mm in width. Additionally, the hosel length of blade-type or muscle-back iron club heads may be approximately 60 mm to 90 mm in length measured from the origin point 132A where the axis at the center of the hosel intersects the ground plane 124 to the center at the top of the hosel 126. Generally, the top lines on a blade-type or muscle-back iron club head are thin and set. For example, the top view from a reference position, a golfer looking down on the club head can see only the thin top surface 112 and the striking face 110, with none of the rear surface 120 being visible.

B. Description of Muscle-Back or Blade-Type Iron Clubs and Club Heads in Accordance with Examples of this Invention FIG. 1 generally illustrates an example muscle-back or blade iron golf club 100 in accordance with at least some examples of this invention. This club 100 includes a club head 102, a shaft 106 (which will be described in more detail below), and a grip member 103 engaged with the shaft 106. While a low loft iron golf club head 102 is illustrated in these figures, aspects of this invention may be applied to any type of iron club head, including, for example: low, middle, and high loft club heads (of any desired loft, e.g., 1-iron, 2-iron, 3-iron, etc. to 9-iron and wedges with loft angles ranging from 20-64 degrees). The iron club heads may be made from any desired materials, in any desired construction and/or in any desired manner, including from conventional materials, in conventional constructions, in conventional manners, as are known and/or used in the art, optionally modified (if necessary, e.g., in size, shape, inclusion of structures, etc.) as required for aspects of this invention as described in more detail below.

Any desired materials also may be used for the shaft 106, including conventional materials that are known and/or used in the art, such as steel, graphite based materials, polymers, composite materials, combinations of these materials, etc. Optionally, if necessary or desired, the shaft 106 may be modified (e.g., in size, shape, etc.) to accommodate releasable club head/shaft connection parts. The grip member 103 may be engaged with the shaft 106 in any desired manner, including in conventional manners that are known and/or used in the art (e.g., via cements or adhesives, via mechanical connections, etc.). Any desired materials may be used for the grip member 103, including conventional materials that are known and/or used in the art, such as rubber, polymeric materials, cork, rubber or polymeric materials with cord or other fabric elements embedded therein, cloth or fabric, tape, etc.

Figure 3:
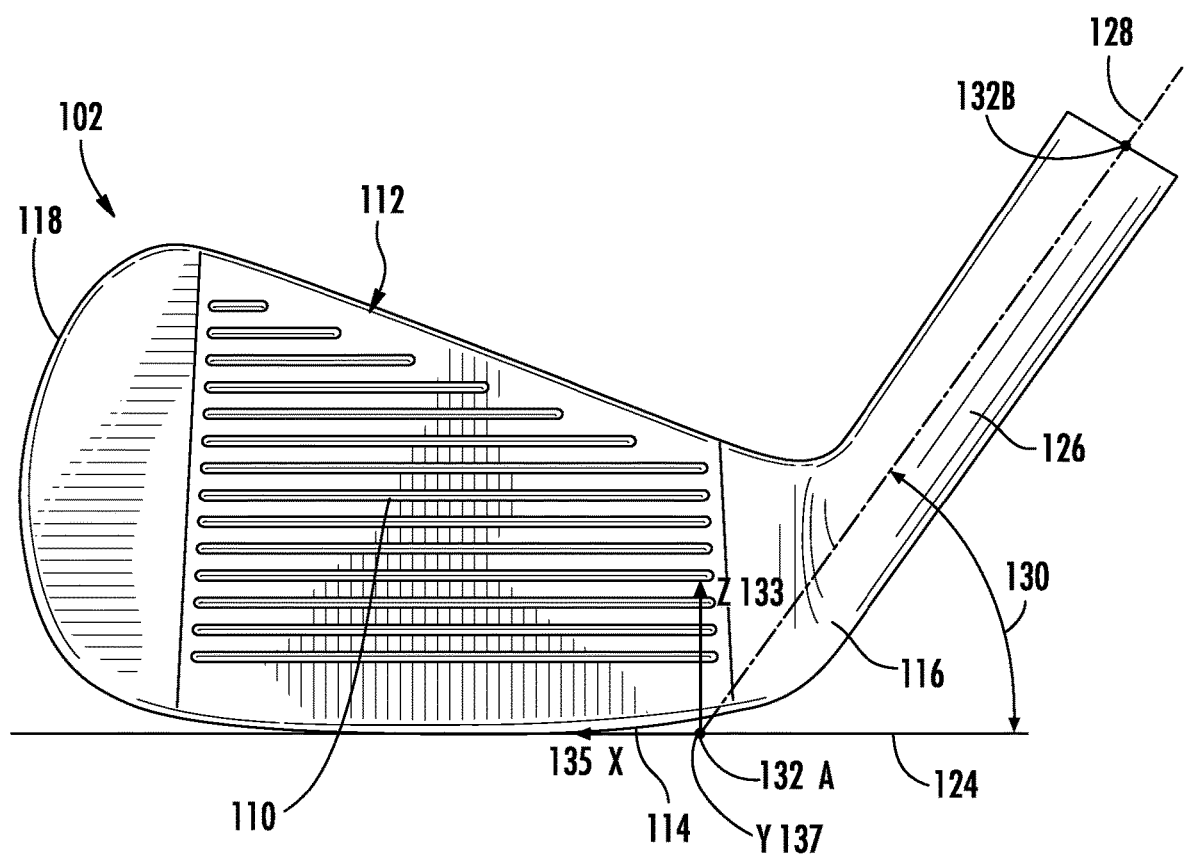
FIGS. 3 through 7B generally illustrate various views of an example golf club head and various performance parameters and characteristics according to this invention.

Generally, all iron club heads 102 include various parts. FIG. 3 illustrates various parts of the golf club head 102 as will be referenced throughout the remainder of this application (as referenced from USGA Rules of Golf). An iron club head 102 has a face or striking face 110, a top surface 112, a sole 114, a heel 116, a toe 118, and a rear surface 120. The top surface 112 may be defined as the upper portion of the head 102. The sole 114 may be defined as the bottom or underside portion of the head 102, and is generally opposite the top surface 112. The sole 114 may include an area on the club head 102 that rests on the ground when a golfer soles the golf club 100. The sole 114 may generally rest on a ground plane 124, wherein the ground plane 124 is a horizontal plane tangent with the bottom of the club head 102. The heel 116 may the part of the club head 102 nearer to and including a hosel 126. The toe 118 may be the area of the golf club 100 that is the farthest from the shaft 106. The rear surface 120 of the club head 102 is generally opposite the face 110. The shaft 106 attaches to the head 102 at the heel 116 via a hosel 126. The shaft 106 has a center axis. The hosel 126 may have a bore for receiving the shaft 106, or a shaft adapter (not shown). The hosel bore has a center axis or a hosel axis 128. If the shaft 106 is inserted and attached directly to hosel bore, the hosel axis 128 may be substantially coincident with shaft axis. For club configurations including a shaft adapter, the shaft 106 may be received in a shaft adapter bore. The shaft adapter bore may have a center axis or shaft adapter axis, which may be substantially coincident with shaft axis. The shaft adapter axis may be offset angularly and/or linearly from the hosel axis 128 to permit adjustment of club parameters via rotation of the shaft adapter with respect to club head 102, as is known by persons skilled in the art.

According to aspects of this invention, a golf club 100 may be oriented in a reference position. In the reference position, the golf club 100 may include a number of parameters or characteristics that may include, but are not limited to: a face center location, a loft angle, a face angle, a lie angle, and a center of gravity location. Parameters or characteristics as well as methods and procedures for measuring them will be described and detailed below.

As illustrated in FIG. 3, a lie angle 130 is defined as the angle formed between the shaft axis or hosel axis 128 and a horizontal plane contacting the sole 114, which may be the ground plane 124 when the iron is positioned such that the scorelines on the face are parallel to the ground plane 124.

Figure 4:
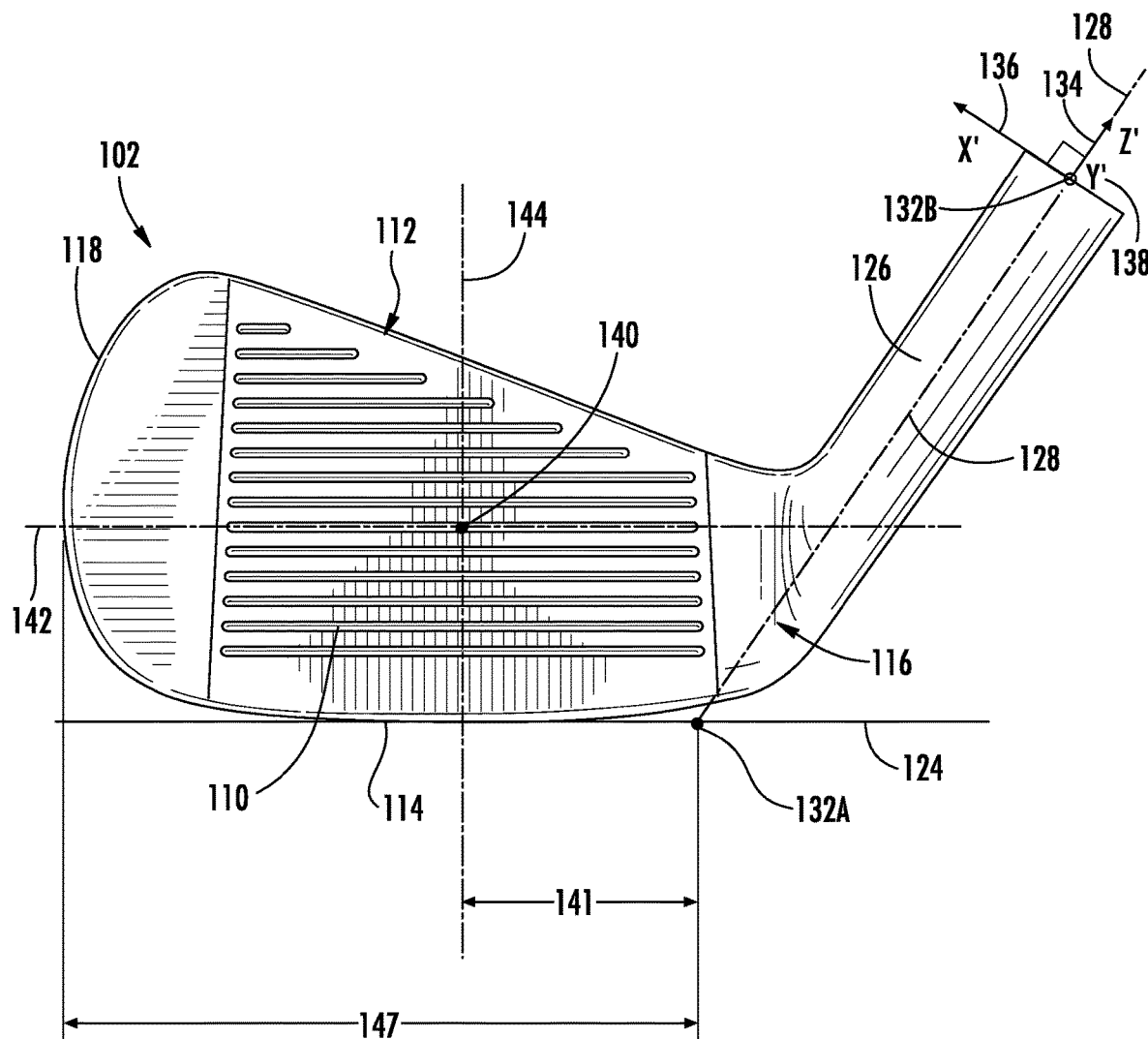

FIG. 4 illustrates the face center location 140 on a fixtured club head 102. The face center 140 is determined using Unites States Golf Association (USGA) standard measuring procedures and methods. For example, the current USGA procedure requires finding the center point along a horizontal line 142 along the club face 110 until the heel 116 and the toe 118 measurements from the edges of the roughened area of the face 110 of the club head 102 are equal. After finding the face center point, the face center plane 144 is defined as a vertical plane through the center point. Then, the center point on a face center plane 144 is found along the club face 110 when the upper portion 112 and the sole 114 measurements at the edges of the face 110 of the club head 102 are also equal. When the heel 116 and the toe 118 measurements are equal and the upper portion 112 and the sole 114 measurements are equal, the intersecting point of these lines is defined as the face center location 140. For irons, the heel and toe measurement is made at the edges of the roughened area of the face.

Figure 5:
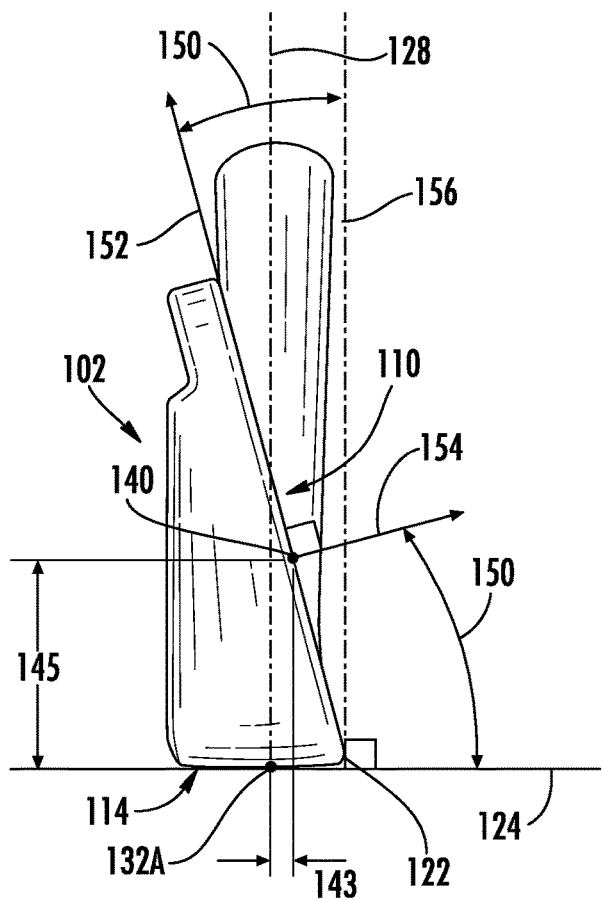

FIG. 5 illustrates an example of a loft angle 150 and a leading edge 122 of the golf club head 102. As illustrated in FIG. 5, the loft angle 150 is defined as a measurement between an axis normal 152 or perpendicular to a face center axis 154 and an axis normal 156 or perpendicular to the ground plane 124. The face center axis 154 is defined as the axis from the face center 140 and normal to the face. Additionally, the loft angle 150 may be defined as a measurement between the face center axis 154 and the ground plane 124. It is recognized that each of these loft angle 150 definitions may yield a similar or exactly the same loft angle measurement. The leading edge 122 is the forward most surface connecting the sole 114 and the striking face 110. The leading edge 122 may be a constant radius or may have a curvature that changes along the heel to the toe of the golf club head.

An origin point 132 may be defined on the golf club 100 or golf club head 102, or a point defined in relation to certain elements of the club or head. Various other points, such as the center of gravity, sole contact, and face center, may be described and/or measured in relation to the origin point 132. FIG. 3 illustrates two different examples of where the origin point 132 may be located. A first location 132A, defined as a ground origin point 132A, is generally located at the ground plane 124. The ground origin point 132A is defined as the point at which the ground plane 124 and the hosel axis 128 intersect. The second location 132B, defined as the hosel origin point 132B, is generally located on the hosel 126. The hosel origin point 132B is located on the hosel axis 128 and coincident with the uppermost edge 126B of the hosel 126. Either location for the origin point 132 may be utilized without departing from this invention. Additionally, other locations for the origin point 132 may be utilized without departing from this invention. Throughout the remainder of this application, the ground origin point 132A will be utilized for all reference locations, tolerances, and calculations.

As illustrated in FIG. 3, a primary coordinate system may be defined on the origin point 132A, e.g., the origin point 132A has an X axis 135 parallel to the ground plane 124 and generally parallel to the leading edge 122 of the golf club head 102, a Y axis 137 perpendicular to the X axis 135 and oriented away from the rear surface of the golf club 120, and a Z axis 133 perpendicular to the ground plane 124.

Additionally, as illustrated in FIG. 4, a secondary coordinate system may be defined on the origin point 132B, e.g., with a Z' axis 134 extending along the direction of the shaft axis 107 (and/or the hosel axis 128), an X' axis 136 parallel with the vertical plane and normal to the Z' axis, and a Y' axis 138 normal to the X' and Z' axes.

Figure 6:
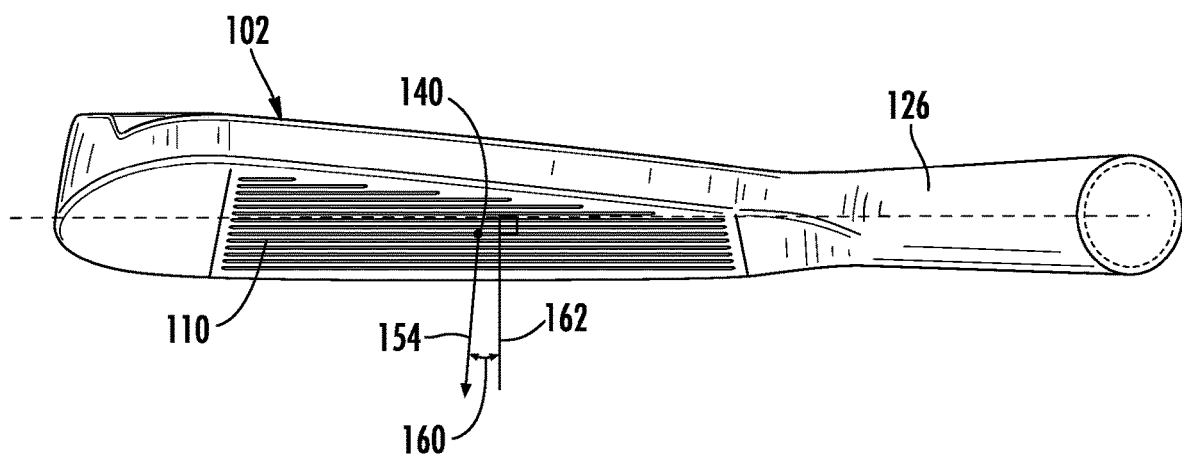

FIG. 6 illustrates an example of a face angle 160 of a golf club head 102. As illustrated in FIG. 6, the face angle 160 is measured by utilizing the face center axis 154 and a right plane 162 (a plane perpendicular to the X axis 135).

Figure 7A:
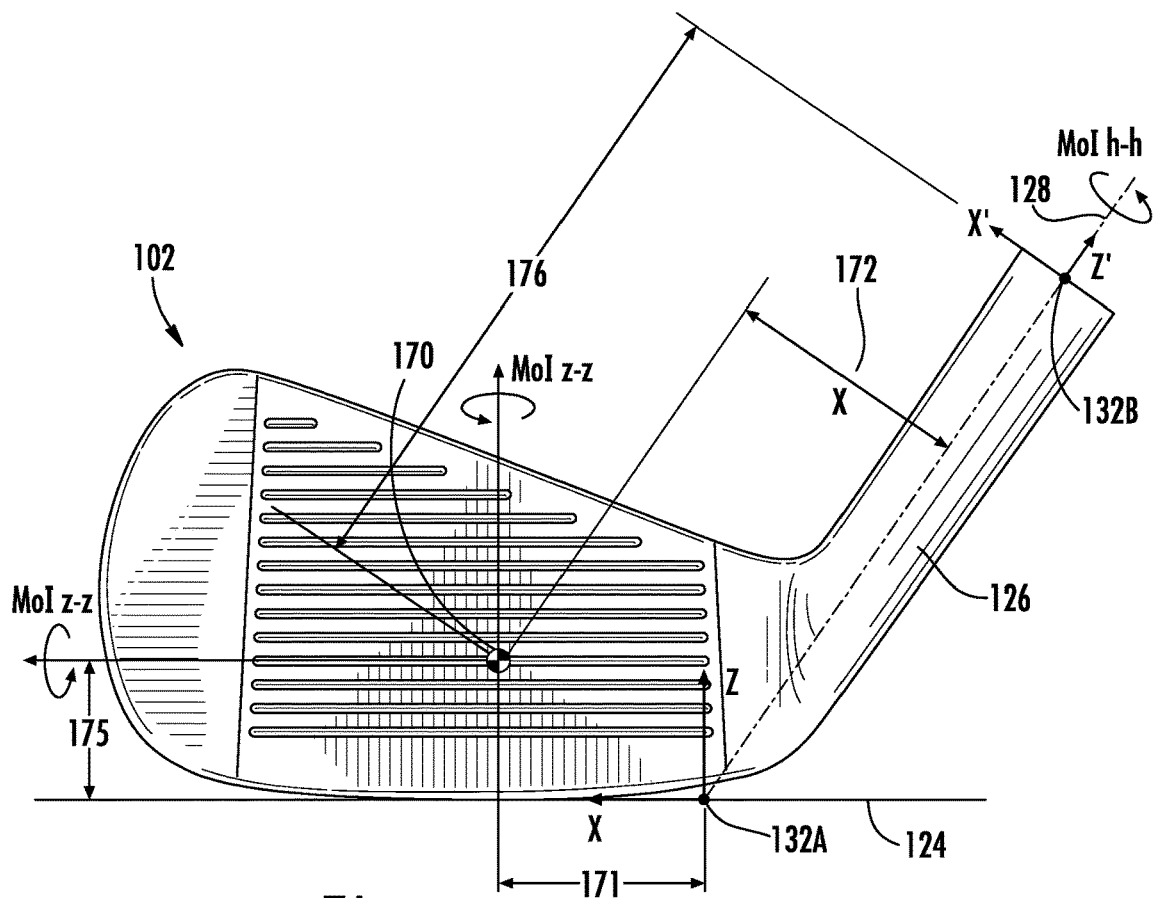
Figure 7B:
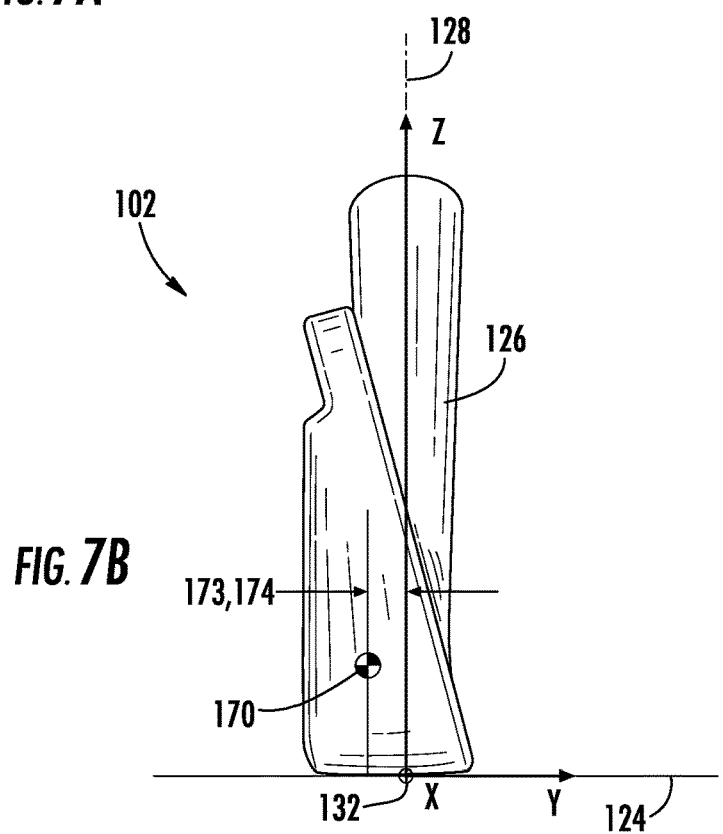

FIGS. 7A and 7B illustrate an example of a center of gravity location 170 as a specified parameter of the golf club head 102. The center of gravity of the golf club head 102 may be determined using various methods and procedures known and used in the art. The golf club head 102 center of gravity location 170 is provided with reference to its position from the origin point 132A. As illustrated in FIGS. 7A and 7B, the center of gravity location 170 is defined by a distance from the origin point 132A along the X axis 135 named CGX 171, Y axis 137 named CGY 173, and Z axis 133 named CGZ 175. The center of gravity 170 of the golf club head 102 may be provided with reference to its position from the hosel origin point 132B. As illustrated in FIGS. 7A and 7B, the center of gravity 170 location may also be defined by a distance from the hosel origin point 132B along the X' axis 136, named AX 172, the Y' axis 138, named AY 174, and the Z' axis 134, named AZ 176.

The moment of inertia is a clubhead property whose importance is well known to one skilled in the art. There are three moment of inertia properties that this application may reference. As FIG. 7A illustrates the MOI x-x, which is the moment of inertia of an axis through the center of gravity of the clubhead around an axis parallel to the X-axis 135 of the origin coordinate system. Similarly, the MOI z-z is the moment of inertia of an axis through the center of gravity around an axis parallel to the Z-axis 133 as illustrated in FIG. 4. Lastly, the MOI h-h, is the moment of inertia around the shaft axis or Z'-axis 134 as illustrated in FIG. 7A. The MOI h-h is important in looking at how the clubhead may resist the golfer's ability to close the clubface during the swing.

Additionally, FIGS. 4 and 5 show the face center location 140 may be defined from the ground origin point 132A and the ground plane coordinate system, where CFX 141 is the distance along the X axis 135 from the origin point 132A, CFY 143 is the distance along the Y-axis 137, and CFZ 145 is distance along the Z-axis 133. Also, the head length 147 of the golf club head can be defined from the origin point 132A as measured along X-axis 135 to the furthest extent of the toe 118 of the golf club head 102.

FIGS. 3-7B illustrate a golf club head 102 oriented in a reference position. In the reference position, the hosel axis 128 or shaft axis lies in a vertical plane as shown in FIG. 5. As illustrated in FIG. 3, the hosel axis 128 may be oriented at a lie angle 130. The lie angle selected for the reference position may be the golf club 100 manufacturer's specified lie angle. If a specified lie angle is not available from the manufacturer, a lie angle can be determined using the parallel scoreline method described herein. Furthermore for the reference position, as illustrated in FIG. 5, the striking face 110 may be oriented at a loft angle 150. The loft angle selected for the reference position may be the golf club manufacturer's specified loft angle. Table 1, below, provides typical loft and lie angles for various blade-type iron golf club heads in accordance with an embodiment of this invention.

TABLE 1

Example Loft and Lie Angle for a Blade-Type Iron Club Heads

| Blade-Type Iron Golf Club Head | Typical Loft Angle | Typical Lie Angle |
|---|---|---|
| #2 | 18.0° | 59.0° |
| #3 | 21.0° | 59.0° |
| #4 | 24.0° | 60.0° |
| #5 | 27.0° | 61.0° |
| #6 | 31.0° | 62.0° |
| #7 | 35.0° | 62.5° |
| #8 | 39.0° | 63.0° |
| #9 | 43.0° | 63.5° |
| PW | 47.0° | 64.0° |

Club head parameters or characteristics may be measured physically, or in a computer-aided-design (CAD) environment. Generally, if a 3 dimensional (3D) model of club head 102 is not readily available, one may be created by performing a 3D scan of the club head 102 and creating a model file from the scan data and/or physical measurements, such that the model is substantially representative of the physical club head. In the CAD environment, the model of club head 102 may be set in the reference position with the face 110 oriented at the manufacturer's loft, lie, and face angles within the CAD environment such that the model is fully constrained.

Additionally, the golf club 100 may be physically oriented in the reference position using a fixturing system known and used in the art. As was described above, the shaft axis may be aligned at a lie angle according to the golf club manufacturer's specification, or at an appropriate lie angle as determined means described above. The golf club head 102 may rest with its sole 114 contacting a horizontal surface 124 with the club face 110 positioned at the manufacturer's face angle and/or loft angle using conventional loft and face angle measurement gauges known to one of skill in the art.

Figure 8:
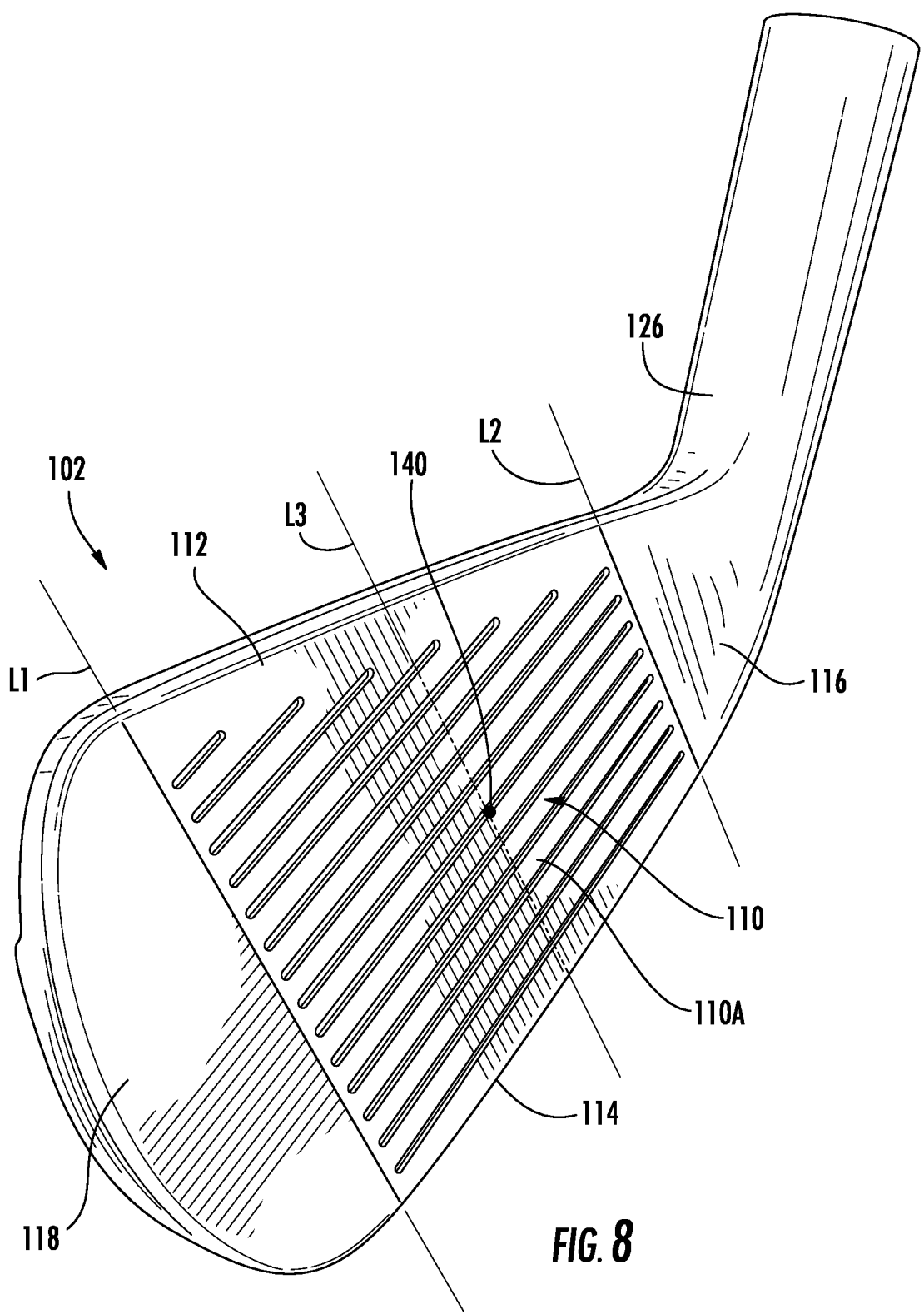
FIG. 8 illustrates a perspective front view of a golf club head according to this invention.
Figure 9:
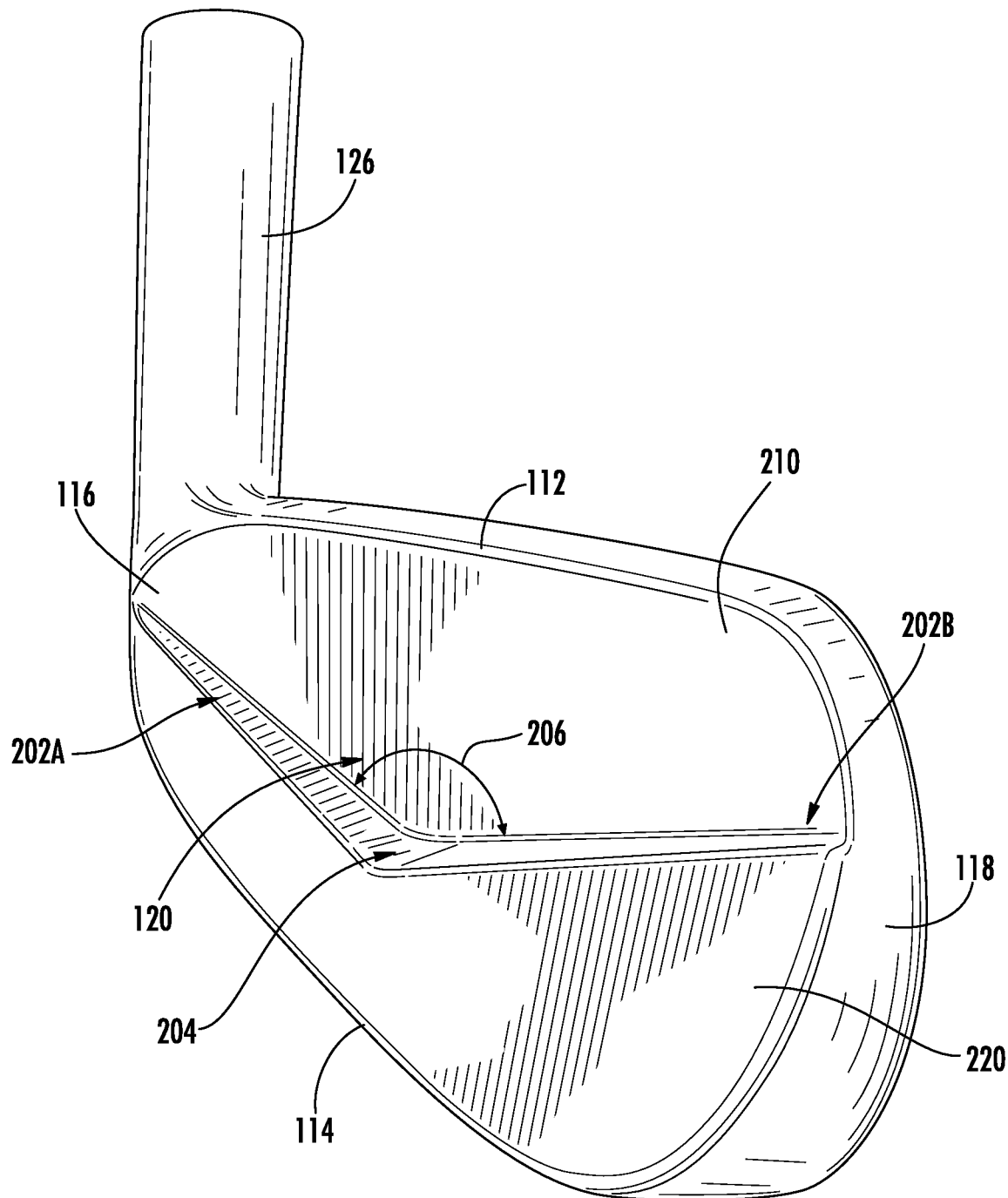
FIG. 9 illustrates a perspective rear view of the golf club head illustrated in FIG. 8 according to this invention.
Figure 10:
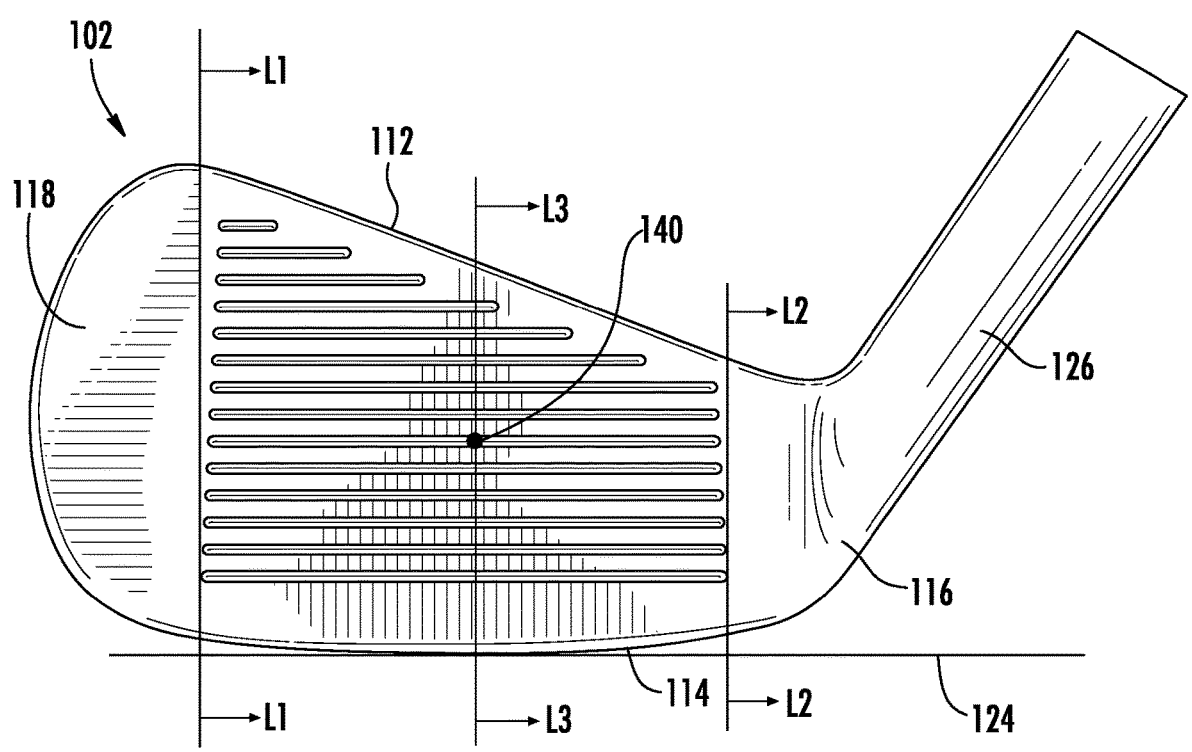
FIG. 10 illustrates a front view of the golf club head illustrated in FIG. 8 according to this invention.
Figure 11:
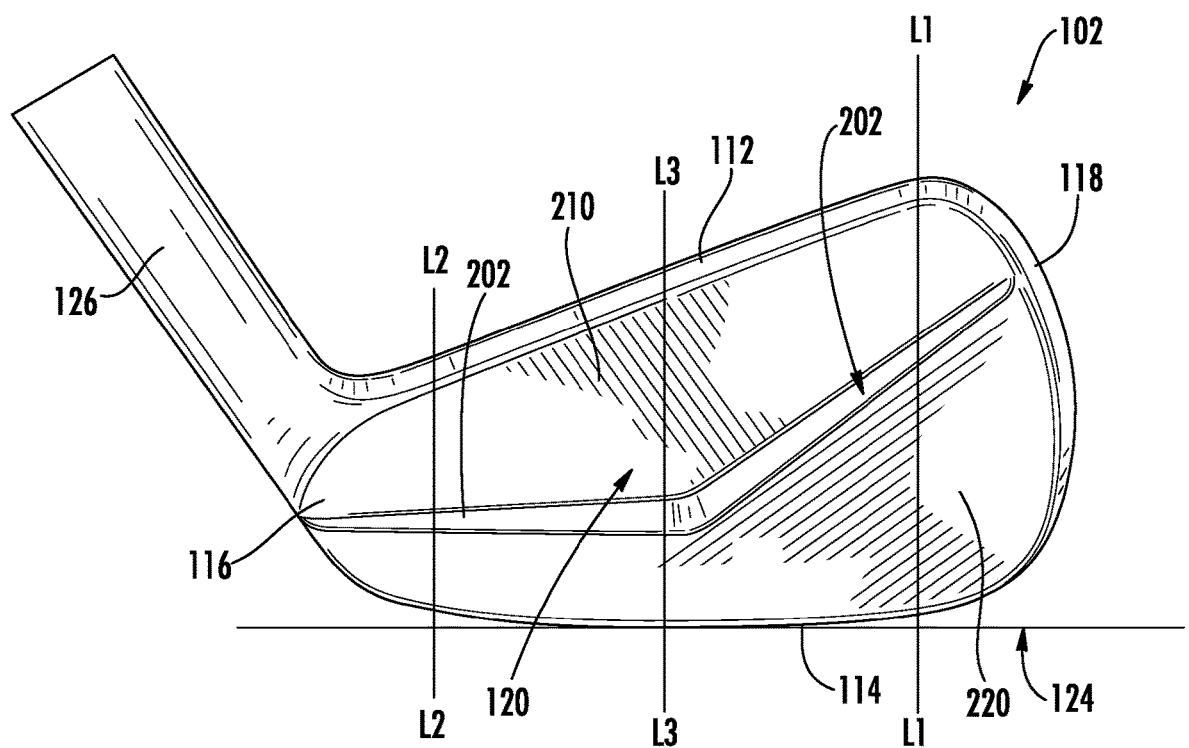
FIG. 11 illustrates a rear view of the golf club head illustrated in FIG. 8 according to this invention.
Figure 12:
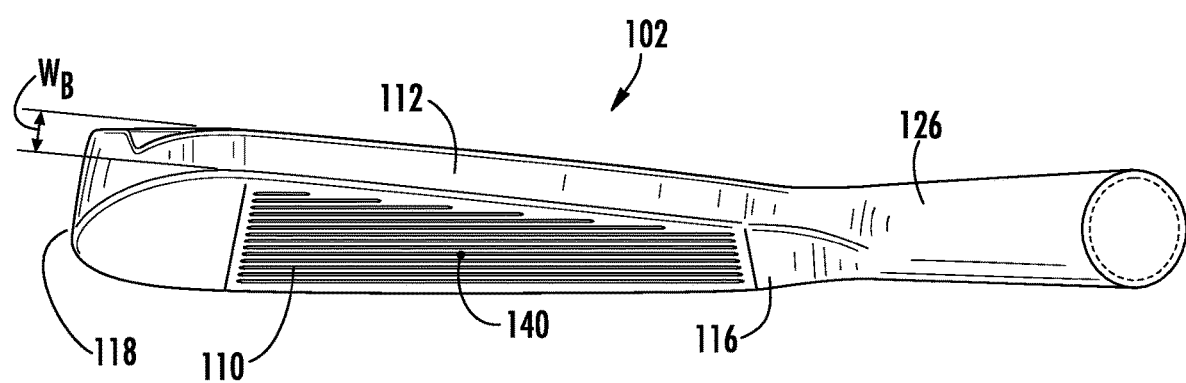
FIG. 12 illustrates a top view of the golf club head illustrated in FIG. 8 according to this invention.
Figure 13:
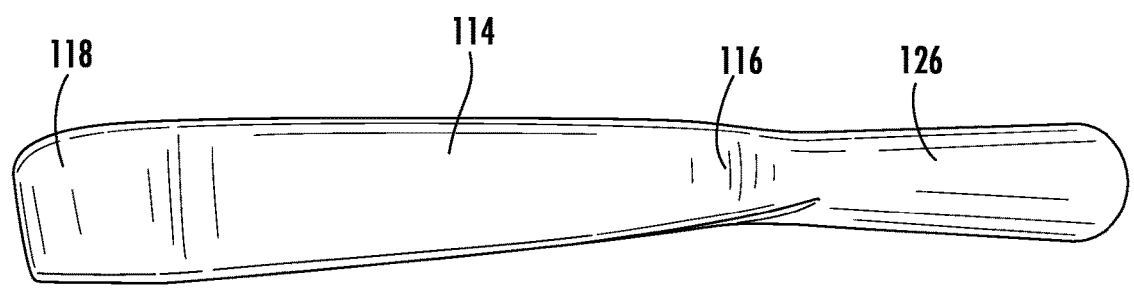
FIG. 13 illustrates a bottom view of the golf club head illustrated in FIG. 8 according to this invention.
Figures 14, 15:
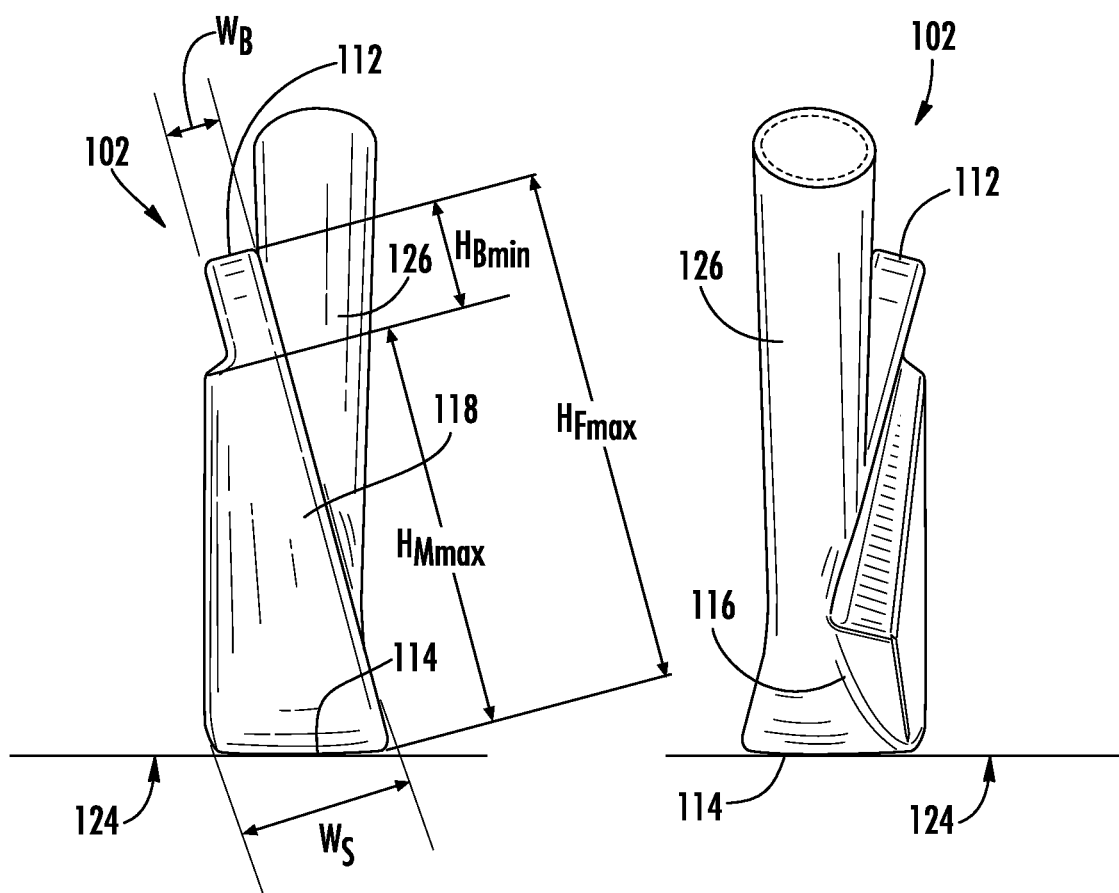
FIG. 14 illustrates a side view (on the toe side) of the golf club head illustrated in FIG. 8 according to this invention.
FIG. 15 illustrates another side view (on the heel side) of the golf club head illustrated in FIG. 8 according to this invention.

The present invention provides a blade-type or muscle-back iron club head. FIGS. 8 through 16C illustrate a blade-type or muscle-back iron club head in accordance with aspects of this invention. FIG. 8 illustrates a perspective front view of the golf club head 102. FIG. 9 illustrates a perspective rear view of the golf club head 102. FIG. 10 illustrates a front view of the golf club head 102. FIG. 11 illustrates a rear view of the golf club head 102. FIG. 12 illustrates a top view of the golf club head 102. FIG. 13 illustrates a bottom view of the golf club head 102. FIG. 14 illustrates a side view (on the toe side) of the golf club head 102. FIG. 15 illustrates another side view (on the heel side) of the golf club head 102. FIGS. 16A through 16C illustrate cross-sectional views along lines L1, L3 and L2 respectively of the golf club head 102.

As described above, the club head 102 includes a face or striking face 110, a top surface 112, a sole 114, a heel 116, a toe 118, and a rear surface 120. The rear surface 120 comprises a substantially flat area, which defines a blade portion 210 of the club head 102, and a thickened area which defines a muscle portion 220 of the club head 102. The blade portion 210 generally occupies the entire upper portion of the club head 102, and has a substantially constant thickness that may be less than, for example, approximately 6 mm. The muscle portion 220 generally constitutes a lower portion of the club head 102, and has a varying thickness that is everywhere greater than that of blade portion 210.

The striking face 110 may be provided with score lines, grooves, or other surface features or textures enhancing the ability of the club head to grip the golf ball during impact. A grip-enhanced area or a ball striking area 110A may be generally defined by a heel-side score line (or other grip-enhancing surface feature) boundary L1 (shown dashed) that is perpendicular to the ground plane 124 and a toe-side score line (or other grip-enhancing surface feature) boundary L2 (shown dashed) that is perpendicular to the ground plane 124 and by segments of the top surface 112 and sole 114 perimeter edges of the striking face 110 extending between by those heel-side and toe-side boundary lines L1, L2. Thus, the ball striking area 110A has a length $L_S$ (extending between boundary L1 and boundary L2) and a height $H_S$ (extending between top surface 112 edge and the leading edge 122). Generally, this height $H_S$ increases in the toe direction. The height $H_S$ may be a minimum at the heel most extent of the ball striking area 110A, and a maximum at some point in the toe direction. A centerline L3 of the ball striking area 110A may be located halfway along the length $L_S$ of the ball striking area 110A along center face plane 144. Lines L1, L2 and L3 may be associated with through-the-thickness cross-sections as illustrated in FIG. 10 and FIGS. 16A-16C, respectively. Thus, points on the rear surface 120 may be defined by reference to lines L1, L2 and/or L3.

As illustrated in FIGS. 9 and 11, the muscle portion 220 adds mass and material to the top surface 112 and toe 118 and removes mass and material from sole 114 and heel 116. This mass distribution of the muscle portion 220 moves the center of gravity 170 of the club head 102 closer to the face center 140 location. For most conventional blade-type irons (as illustrated in FIGS. 2A and 2B), the center of gravity 170 is located on the heel and sole side of the face center location 140 and approximately 2 to 3 mm away from the face center plane 144 location in the X-axis direction. For the club heads 102 in accordance with aspects of this invention with the sloped muscle portion 220, the center of gravity 170 moves towards the toe side of the club head by approximately 0.5 to 1.0 mm closer to the face center plane 144. This is an approximate 17% to 50% change in the location of the center of gravity 170 with respect to the face center plane 144, moving the center of gravity 170 17 to 50% closer to the face center 140 as compared to the conventional blade-type irons.

As illustrated in FIGS. 9 and 11, the muscle portion 220 of the club head 102 is larger or has a greater height at the toe as compared to the heel. The area and the mass of the muscle portion 220 increases as the muscle portion 220 extends from the heel to the toe. The height of the muscle portion 220 increases extending across the rear surface from the heel to the toe. Additionally, the height of the muscle portion 220 generally increases at a greater rate from the middle of the club head 102 at approximately L3 to the toe of the club head 102 at approximately L1 as compared to the heel of the club head 102 at approximately L2 to the middle of the club head 102 at approximately L3.

The muscle portion 220 may be separated from the upper blade portion 210 by a blade interface 202. The blade interface 202 may be a smooth, arcuate surface forming the transition area between the upper blade portion 210 and the muscle portion 220. The blade interface 202 may extend across the rear surface 120 of the club head 102 from the heel 116 to the toe 118. In an aspect of the invention, there may be no distinct boundary separating the muscle portion 220 and the upper blade portion 210, wherein the transition between the muscle portion 220 and the upper blade portion 210 may occur via a gradual surface curvature.

As illustrated in FIGS. 9 and 11, the blade interface 202 includes a first blade interface 202A and a second blade interface 202B. The first blade interface 202A and the second blade interface 202B are not along the same line. The first blade interface 202A and the second blade interface 202B may be intersecting lines, intersecting at a convergence point 204. The convergence point 204 may be located along or near to the face center plane 144 of the ball striking area 110A. The first blade interface 202A may extend from the heel 116 to the convergence point 204. The second blade interface 202B may extend from the convergence point 204 to the toe 118. The first blade interface 202A may extend generally parallel to the sole 114 or the leading edge 122 or to the ground plane 124. The second blade interface 202B may then extend from the convergence point at an angle 206 upward toward the toe 118 and the top surface 112.

The angle 206 may be an obtuse angle in accordance with aspects of this invention. For example, the angle 206 may be approximately 125 degrees. In another exemplary embodiment, the angle 206 may be between approximately 105 and 155 degrees. The convergence point 204 is located at a position in the X-axis direction from the ground plane origin 132A to the convergence point 204 between 28 to 34 mm. Table 2 shows an exemplary embodiment of the location of the muscle corner and the angle 206 of the muscle throughout the set.

TABLE 2

Example Muscle Convergence Point Location and Angle Dimensions for 3-, 6-, and 9-Iron Club Heads

| Iron | Location of Convergence Point (ref # 204) [mm] | Angle of Muscle (ref # 206) |
|---|---|---|
| 3 | 32.2 | 120 |
| 6 | 32.2 | 124 |
| 9 | 32.3 | 127 |

As illustrated in FIGS. 16A, 16B, and 16C, the club head 102 may include three different heights, a muscle height $H_M$, a blade height $H_B$, and a face height $H_F$. Each of these heights as illustrated in FIGS. 16A, 16B, and 16C may be defined or measured across the club head at various cross-sections, such as at the toe L1, heel L2 or the face center L3.

As illustrated in FIGS. 11, 16A, 16B, and 16C, the lower muscle portion 220 may include a muscle height $H_M$. The muscle height $H_M$ may be measured parallel to the striking face from the leading edge 122 to the corner of intersection of the lower muscle surface 220 and the blade interface surface 202. Since most clubs will have a small fillet radius at the corner and not a sharp edge, the measurement will be taken to the midpoint of the radius. The muscle height $H_M$ of the muscle portion 220 may vary across the rear surface 112 of the club head 102. The muscle height $H_M X$ may be defined or measured across the club head, where X corresponds to the appropriate cross-section L1, L2, or L3.

For example, the muscle height $H_{M1}$ of a 3-iron or 21-degree loft club head at L1 or near the toe may be approximately 28.2 mm. The muscle height $H_{M2}$ of a 3-iron or 21-degree loft club head at L2 or near the heel may be approximately 12.6 mm. The muscle height $H_{M3}$ 220 of a 3-iron or 21-degree loft club head at L3 or near the face center 140 may be approximately 15.2 mm. Additionally, for example, the muscle height $H_{M1}$ of a 6-iron or 31-degree loft club head at L1 or near the toe may be approximately 31.3 mm. The muscle height $H_{M2}$ of a 6-iron or 31-degree loft club head at L2 or near the heel may be approximately 14.2 mm. The muscle height $H_{M3}$ of a 6-iron or 31-degree loft club head at L3 or near the face center 140 may be approximately 16.4 mm. Additionally, for example, the muscle height $H_{M1}$ of a 9-iron or 43-degree loft club head at L1 or near the toe may be approximately 37.8 mm. The muscle height $H_{M2}$ of a 9-iron or 43-degree loft club head at L2 or near the heel may be approximately 16.5 mm. The muscle height $H_{M3}$ of a 9-iron or 43-degree loft club head at L3 or near the face center 140 may be approximately 20.1 mm. These dimensions are summarized below in Table 3A for an exemplary 3-, 6-, and 9-iron or 21, 31, 43-degree loft blade type club head respectively in accordance with an embodiment of this invention.

TABLE 3A

Summary of Dimensions for Muscle Height $H_M$ for an Exemplary 3-, 6-, and 9-Iron Club Head in Accordance with this Invention

| Iron | Muscle Height at the Toe, $H_{M1}$ [mm] | Muscle Height at the Heel, $H_{M2}$ [mm] | Muscle Height at the Face Center, $H_{M3}$ [mm] |
|---|---|---|---|
| 3 | 28.2 | 12.6 | 15.2 |
| 6 | 31.3 | 14.2 | 16.4 |
| 9 | 37.8 | 16.5 | 20.1 |

The muscle height at the toe $H_{M1}$ may be generally greater than the muscle height at the heel $H_{M2}$. For example, a muscle height toe-heel percentage may be the percentage increase of the muscle height of the toe $H_{M1}$ over the muscle height of the heel $H_{M2}$, or $(H_{M2}-H_{M1})/H_{M1}$. For an exemplary 3-iron golf club head, the muscle height toe-heel percentage may be approximately 123%. For an exemplary 6-iron golf club head, the muscle height toe-heel percentage may be approximately 120%. For an exemplary 9-iron golf club head, the muscle height toe-heel percentage may be approximately 128%. The muscle height toe-heel percentage may range from 75% to 150%. In another embodiment, the muscle height toe-heel percentage may be greater than 150%.

In another example, a muscle height toe-heel ratio may be the ratio of the muscle height of the toe $H_{M1}$ over the muscle height of the heel $H_{M2}$, or $H_{M2}/H_{M1}$. For an exemplary 3-iron golf club head, the muscle height toe-heel ratio may be approximately 2.2. For an exemplary 6-iron golf club head, the muscle height toe-heel ratio may be approximately 2.2. For an exemplary 9-iron golf club head, the muscle height toe-heel ratio may be approximately 2.3. The muscle height toe-heel ratio may range from 1.5 to 3. In another embodiment, the muscle height toe-heel ratio may be greater than 3.

As illustrated in FIGS. 16A, 16B, and 16C, the upper blade portion 210 may include a blade height $H_B$. The blade height $H_B$ may be measured parallel to the striking face from the corner of intersection of the lower muscle surface 220 and the blade interface surface 202 to the top surface 112. Since most clubs will have a small fillet radius at the corner and not a sharp edge, the measurement will be taken to the midpoint of the radius. The blade height $H_B$ of the blade portion 210 may vary across the rear surface 112 of the club head 102. The blade height $H_{BX}$ may be defined or measured across the club head, where X corresponds to the appropriate cross-section L1, L2, or L3.

For example, the blade height $H_{B1}$ of a 3-iron or 21-degree loft club head at L1 or near the toe may be approximately 21.5 mm. The blade height $H_{B2}$ of a 3-iron or 21-degree loft club head at L2 or near the heel may be approximately 16.6 mm. The blade height $H_{B3}$ of a 3-iron or 21-degree loft club head at L3 or near the face center 140 may be approximately 25.8 mm. Additionally, for example, the blade height $H_{B1}$ of a 6-iron or 31-degree loft club head at L1 or near the toe may be approximately 20.4 mm. The blade height $H_{B2}$ of a 6-iron or 31-degree loft club head at L2 or near the heel may be approximately 16.6 mm. The blade height $H_{B3}$ of a 6-iron or 31-degree loft club head at L3 or near the face center 140 may be approximately 26.4 mm. Additionally, for example, the blade height $H_{B1}$ of a 9-iron or 43-degree loft club head at L1 or near the toe may be approximately 17.7 mm. The blade height $H_{B2}$ of a 9-iron or 43-degree loft club head at L2 or near the heel may be approximately 17.3 mm. The blade height $H_{B3}$ of a 9-iron or 43-degree loft club head at L3 or near the face center 140 may be approximately 28.8 mm. These dimensions are summarized below in Table 3B for an exemplary 3-, 6-, and 9-iron or 21, 31, 43-degree loft blade type club head respectively in accordance with an embodiment of this invention.

TABLE 3B

Summary of Dimensions for Blade Height $H_B$ for an Exemplary 3-, 6-, and 9-Iron Club Head in Accordance with this Invention

| Iron | Blade Height at the Toe, $H_{B1}$ [mm] | Blade Height at the Heel, $H_{B2}$ [mm] | Blade Height at the Face Center, $H_{B3}$ [mm] |
|---|---|---|---|
| 3 | 21.5 | 16.6 | 25.8 |
| 6 | 20.4 | 16.6 | 26.4 |
| 9 | 17.7 | 17.3 | 28.8 |

As illustrated in FIGS. 16A, 16B, and 16C, the club head 102 may include a face height $H_F$. The face height $H_F$ may be measured from the leading edge 122 to the top surface 112 parallel to the loft plane of the golf club head. Since most clubs will have a small fillet radius at the corner and not a sharp edge, the measurement will be taken to the midpoint of the radius. The face height $H_F$ may vary across the rear surface 112 of the club head 102. The face height $H_F X$ may be defined or measured across the club head, where X corresponds to the appropriate cross-section L1, L2, or L3.

For example, the face height $H_{F1}$ of a 3-iron or 21-degree loft club head at L1 or near the toe may be approximately 49.7 mm. The face height $H_{F2}$ of a 3-iron or 21-degree loft club head at L2 or near the heel may be approximately 29.2 mm. The face height $H_{F3}$ of a 3-iron or 21-degree loft club head at L3 or near the face center 140 may be approximately 41.0 mm. Additionally, for example, the face height $H_{F1}$ of a 6-iron or 31-degree loft club head at L1 or near the toe may be approximately 51.7 mm. The face height $H_{F2}$ of a 6-iron or 31-degree loft club head at L2 or near the heel may be approximately 30.8 mm. The face height $H_{F3}$ of a 6-iron or 31-degree loft club head at L3 or near the face center 140 may be approximately 42.8 mm. Additionally, for example, the face height $H_{F1}$ of a 9-iron or 43-degree loft club head at L1 or near the toe may be approximately 55.5 mm. The face height $H_{F2}$ of a 9-iron or 43-degree loft club head at L2 or near the heel may be approximately 33.8 mm. The face height $H_{F3}$ of a 9-iron or 43-degree loft club head at L3 or near the face center 140 may be approximately 48.9 mm. These dimensions are summarized below in Table 3C for an exemplary 3-, 6-, and 9-iron or 21, 31, 43-degree loft blade type club head respectively in accordance with an embodiment of this invention.

TABLE 3C

Summary of Dimensions for Face Height $H_F$ for an Exemplary 3-, 6-, and 9-Iron Club Head in Accordance with this Invention

| Iron | Face Height at the Toe, $H_{F1}$ [mm] | Face Height at the Heel, $H_{F2}$ [mm] | Face Height at the Face Center, $H_{F3}$ [mm] |
|---|---|---|---|
| 3 | 49.7 | 29.2 | 41.0 |
| 6 | 51.7 | 30.8 | 42.8 |
| 9 | 55.5 | 33.8 | 48.9 |

Furthermore, the lower muscle portion 220 may be defined having an average muscle height $H_{MAVG}$ (measured from the blade interface 202 to the leading edge 122) extending from the heel to the toe. Additionally, the muscle portion 220 may be defined having an average heel muscle height $H_{M(L2-L3)}$ extending between the heel-side score line L2 and the face center score line L3. Additionally, the muscle portion 220 may be defined having an average toe muscle height $H_{M(L3-L1)}$ extending between the face center score line L3 and the toe-side score line L1. Exemplary dimensions of average muscle height are summarized below in Table 4A for an exemplary 3-, 6-, and 9-iron or 21, 31, 43-degree loft blade type club head respectively in accordance with an embodiment of this invention.

TABLE 4A

Summary of Average Muscle Height for an Exemplary 3-, 6-, and 9-Iron Club Head in Accordance with this Invention

| Iron | Average Muscle Height, $H_{MAVG}$ [mm] | Average Heel Muscle Height, $H_{M(L2-L3)}$ [mm] | Average Toe Muscle Height, $H_{M(L3-L1)}$ [mm] |
|---|---|---|---|
| 3 | 20.4 | 13.9 | 21.7 |
| 6 | 22.8 | 15.3 | 23.9 |
| 9 | 27.2 | 18.3 | 28.9 |

Additionally, the upper blade portion 210 may be defined having an average blade height $H_{BAVG}$. Generally, the average blade height $H_{BAVG}$ may be defined as the average distance measured from the blade interface 202 to the top surface 112 and extending from the heel to the toe. Additionally, the upper blade portion 210 may be defined having an average heel blade height $H_{B(L2-L3)}$. Generally, the average heel blade height $H_{B(L2-L3)}$ may be defined as average distance measured from the blade interface 202 to the top surface 112 and extending between the heel-side score line L2 and the face center score line L3. Additionally, the upper blade portion 210 may be defined having an average toe blade height $H_{B(L3-L1)}$. Generally, the average toe blade height $H_{B(L3-L1)}$ may be defined as average distance measured from the blade interface 202 to the top surface 112 and extending between the face center score line L3 and the toe-side score line L1. Exemplary dimensions of average blade height are summarized below in Table 4B for an exemplary 3-, 6-, and 9-iron or 21, 31, 43-degree loft blade type club head respectively in accordance with an embodiment of this invention.

TABLE 4B

Summary of Average Blade Height for an Exemplary 3-, 6-, and 9-Iron Club Head in Accordance with this Invention

| Iron | Average Blade Height, $H_{BAVG}$ [mm] | Average Heel Blade Height, $H_{B(L2-L3)}$ [mm] | Average Toe Blade Height, $H_{B(L3-L1)}$ [mm] |
|---|---|---|---|
| 3 | 19.0 | 21.2 | 23.6 |
| 6 | 18.5 | 21.5 | 23.4 |
| 9 | 17.5 | 23.0 | 23.2 |

As illustrated in FIGS. 11, 16A, 16B, and 16C, the lower muscle portion 220 may have a muscle thickness or muscle width $W_M$ at each of the locations of the heel, center and toe. The width at each location is identified as $W_{MX}$, where X corresponds to the appropriate cross-section L1, L2, or L3. $W_{MX}$ is measured perpendicular from the striking face to the corner of intersection of the lower muscle surface 220 and the blade interface surface 120 at the designated cross-section. Since most clubs will a small fillet radius at the corner and not a sharp edge, the measurement will be taken to the midpoint of the radius.

Additionally, the lower muscle portion 220 may have a sole thickness or sole width $W_S$ at each of the locations of the heel, center and toe. The width at each location is identified as $W_{SX}$, where X corresponds to the appropriate number depending upon the measurement at cross-section L1, L2, or L3. $W_{SX}$ is measured perpendicular from the striking face to the leading edge 122. The sole width $W_{SX}$ may range from approximately 8 mm to approximately 16 mm across the rear surface extending from the heel to the toe. FIGS. 16A through 16C illustrate the muscle portion 220 thickness WM at each of the cross-sections L1, L2, and L3. Tables 5A and 5B below summarize exemplary embodiments of the 3-iron, 6-iron, and 9-iron and their muscle width, $W_{MX}$, and sole width, $W_{SX}$.

TABLE 5A

Example Dimensions for Muscle Width Dimensions for a 3-, 6- and 9-Iron Club Heads

| Iron | Muscle Width at the Toe, $W_{M1}$ [mm] | Muscle Width at the Heel, $W_{M2}$ [mm] | Muscle Width at the Mid, $W_{M3}$ [mm] |
|---|---|---|---|
| 3 | 8.8 | 7.6 | 10.1 |
| 6 | 9.1 | 8.0 | 11.4 |
| 9 | 8.9 | 8.0 | 11.1 |

TABLE 5B

Example Dimensions for Sole Width Dimensions for a 3-, 6- and 9-Iron Club Heads

| Iron | Sole Width at the Toe, $W_{S1}$ [mm] | Sole Width at the Heel, $W_{S2}$ [mm] | Sole Width at the Mid, $W_{S3}$ [mm] |
|---|---|---|---|
| 3 | 16.1 | 11.6 | 14.6 |
| 6 | 16.1 | 11.5 | 14.9 |
| 9 | 16.0 | 11.5 | 14.9 |

As illustrated in FIGS. 12 and 14, the upper blade portion 210 may have an average thickness or blade width $W_B$ (measured from the rear surface 120 to the striking face 110) extending from the heel 116 to the toe 118. For example, an average thickness or blade width $W_B$ for the upper blade portion 210 may be approximately 6.5 mm.

Additionally, the lower muscle portion 220 may be defined as having a muscle surface area of the muscle portion. The muscle surface area may be divided between a heel muscle surface area and a toe muscle surface area. The heel muscle surface area may be defined as the surface area of the muscle portion between the heel-side boundary line L1 and the face center plane 144 or L3. The toe muscle surface area may be defined as the surface area of the muscle portion between the toe-side boundary line L2 and the face center plane 144 or L3. For example, the heel surface area of the muscle portion 220 of a 3-iron or 21-degree loft club head may be approximately 328 mm². While, the toe surface area of the muscle portion 220 of a 3-iron or 21-degree loft club head may be approximately 725 mm². Further, the total surface area of the back of the muscle 220 of a 3-iron or 21-degree loft club head may be between 900 and 1200 mm². Approximately 30% of the total surface area of the muscle 220 may be defined on the heel side of the golf club head and correspondingly 70% of the total surface area of the muscle 220 may be defined on the toe side of the golf club head. In another embodiment, approximately 25% to 35% of the total surface area of the muscle 220 may be defined on the heel side of the golf club head and correspondingly 75% to 65% of the total surface area of the muscle may be defined on the toe side of the golf club head. Table 6 below summarizes the surface area of exemplary 3-, 6-, and 9-iron golf club heads in accordance with aspects of this invention.

TABLE 6

Example Dimensions for Surface Area for 3-, 6- and 9-Iron Club Heads

| Iron | Heel Side Surface Area [mm²] | Toe Side Surface Area [mm²] | Total Surface Area of Muscle Portion [mm²] | Heel Surface Area— % of Total Surface Area | Toe Surface Area— % of Total Surface Area |
|---|---|---|---|---|---|
| 3 | 328 | 725 | 1053 | 31% | 69% |
| 6 | 294 | 698 | 992 | 30% | 70% |
| 9 | 325 | 761 | 1086 | 30% | 70% |

Figure 17:
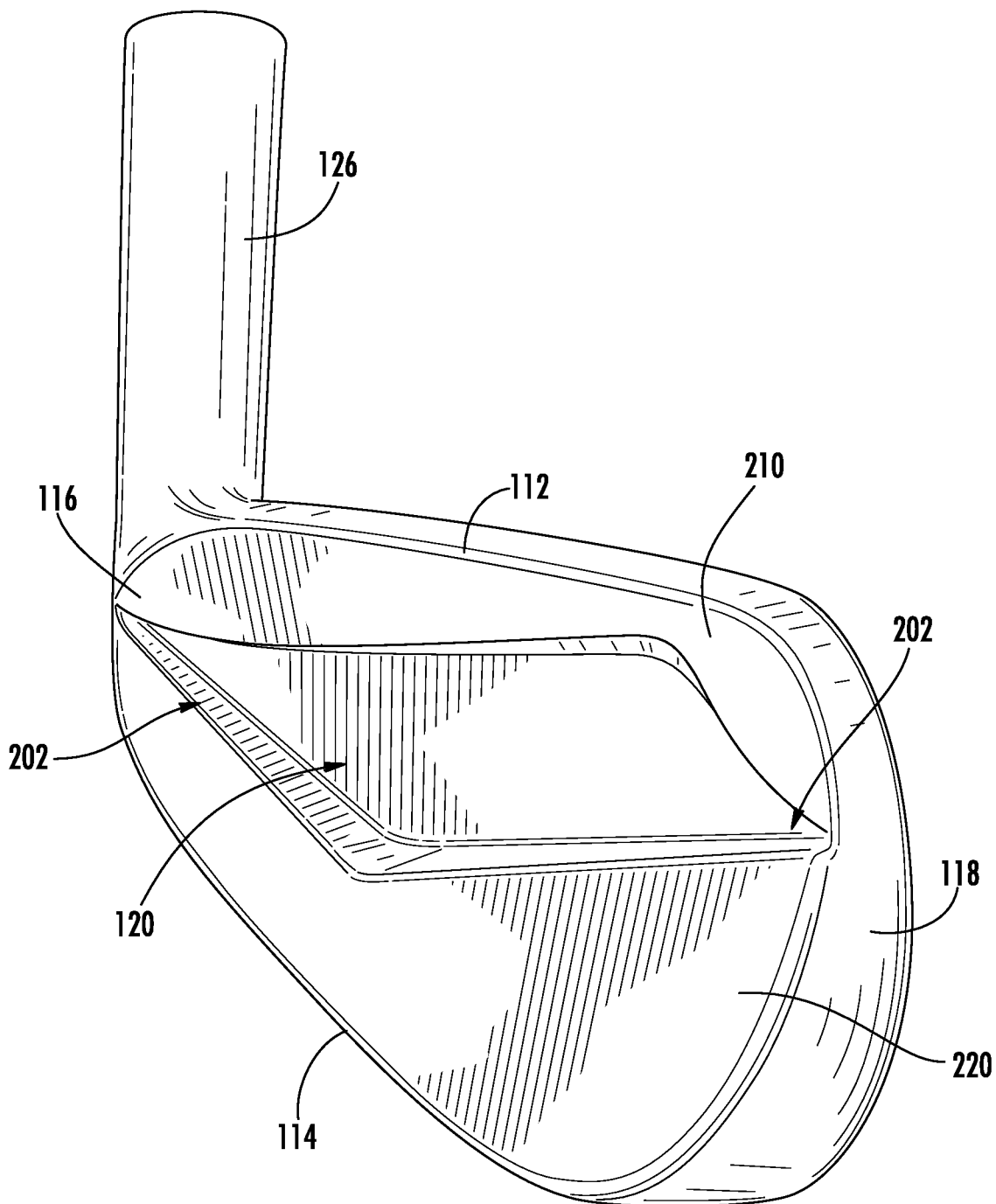
FIG. 17 illustrates a perspective rear view of another golf club head according to this invention.
Figure 18:
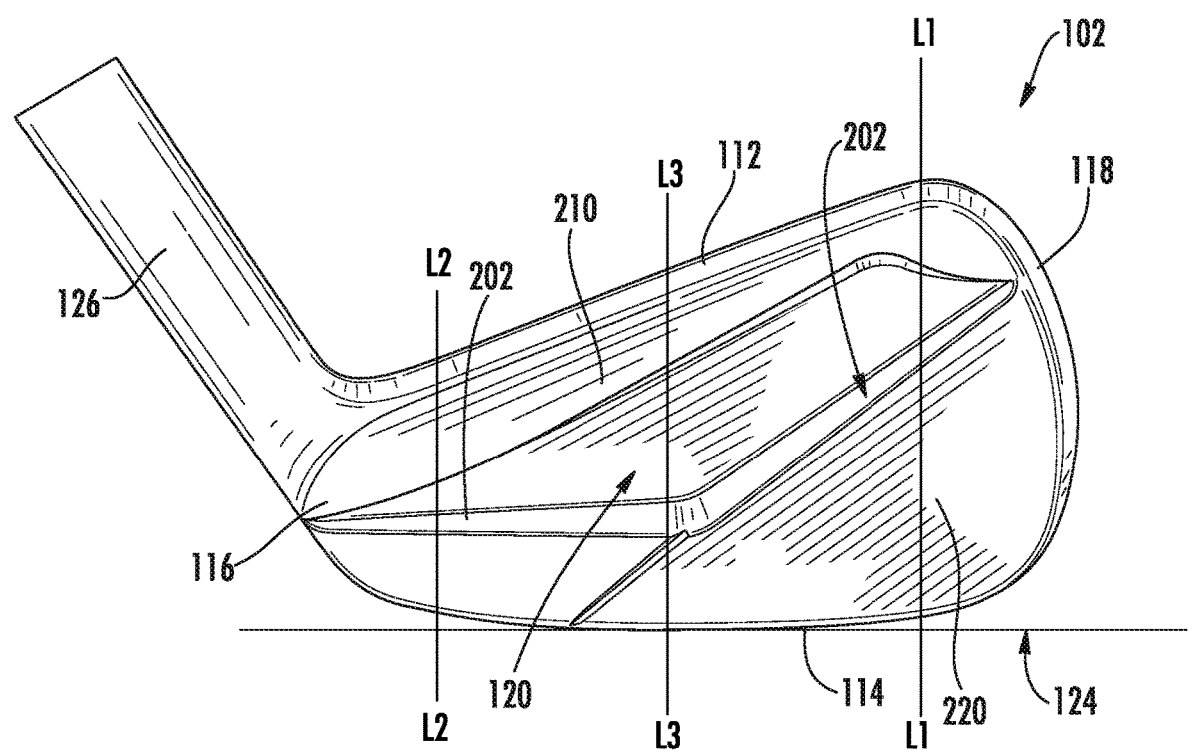
FIG. 18 illustrates a rear view of the golf club head illustrated in FIG. 17 according to this invention.

FIGS. 17 and 18 illustrate another blade-type iron club head in accordance with this invention. As illustrated in FIGS. 17 and 18, a rear surface 120 of the club head 102 may include an indentation positioned within the upper blade portion 210 of the club head 102.

Benefits

Embodiments of this invention present many benefits to the golf industry and the different participants in the golf industry.

First, the mass distribution of the muscle portion moves the center of gravity of the club head closer to the face center location. As was described above, for most conventional blade-type irons, the center of gravity is located to the heel side and sole side of the face center location and approximately 3 mm away from the face center location. For the club heads in accordance with aspects of this invention with the sloped muscle portion, the center of gravity moves towards the toe and top surface of the club head and approximately 0.5 to 1.0 mm closer to the face center location. This is an approximate 17% to 50% change in the location of the center of gravity with respect to the face center, moving the center of gravity 17% to 50% closer to the face center as compared to the conventional blade-type irons. By placing the center of gravity closer to the face center location, the impact efficiency is improved which can improve the ball speed, the vertical and horizontal launch angles, and the corresponding back spin and side spin rates of the golf ball. If this efficiency is improved, the distance and accuracy of the golf shot will be improved. Table 7 below illustrates example dimensions from the ground origin point 132A in the ground coordinate system for the center of gravity locations and the moment of inertia for exemplary 3-, 6-, and 9-iron club heads in accordance with this invention. Table 8 below illustrates example dimensions from the hosel origin point 132B in the hosel coordinate system for the center of gravity locations and the moment of inertia for exemplary 3-, 6-, and 9-iron club heads in accordance with this invention.

TABLE 7

Example Dimensions from Ground Origin Point 132A in Ground Coordinate System for Center of Gravity Locations and Moment of Inertia for a 3-, 6-, and 9-Iron Club Head (Absolute Values of CG Dimensions Shown)

| Iron | CG X [mm] [+/−2 mm] | CGY [mm] [+/−2 mm] | CGZ [mm] [+/−2 mm] | MOI x-x [g*cm$^2$] [+/−400] | MOI z-z [g*cm$^2$] [+/−400] |
|---|---|---|---|---|---|
| 3 | 28.3 | 5.2 | 19.4 | 2580 | 2230 |
| 6 | 29.1 | 7.4 | 19.3 | 2630 | 2310 |
| 9 | 29.3 | 10.3 | 19.0 | 2708 | 2500 |

TABLE 8

Example Dimensions from Hosel Origin Point 132B in Hosel Coordinate System for Center of Gravity Locations and Moment of Inertia for a 3-, 6-, and 9-Iron Club Head (Absolute Values of CG Dimensions Shown)

| Iron | Delta X [mm] [+/−2 mm] | Delta Y [mm] [+/−2 mm] | Delta Z [mm] [+/−2 mm] | MOI h-h [g*cm$^2$] [+/−2 mm] |
|---|---|---|---|---|
| 3 | 34.3 | 5.2 | 66.5 | 4420 |
| 6 | 34.7 | 7.4 | 65.6 | 4950 |
| 9 | 34.7 | 10.3 | 65.1 | 5600 |

In addition to improved mass distribution, this muscle configuration provides unexpectedly a change in modal frequencies, resulting in improved feel and sound when impacting a golf ball. It has been found that increasing the amount of mass in the high-toe region of a blade type iron as taught herein increases the overall structural stiffness of the head, resulting in a higher first non-rigid body mode natural frequency when compared to a traditional muscle blade design of the same sized face, hosel, and sole profile. Correspondingly, the reduced muscle height proximate the center of the club head creates a lower second mode natural frequency when compared to a traditional muscle blade design of the same sized face, hosel, and sole profile. Table 9 displays the predicted natural frequencies computed using finite element analysis of the first three non-rigid body modes of two configurations of a 7-iron of the golf club as taught herein compared to its corresponding traditional muscle blade design 7-iron. Both of the first two modes have frequencies within the more sensitive human hearing range of 2000 Hz to 5000 Hz. The improved blade design leads to a unique overall audible response that is perceived by the golfer as an improved feel during impact.

TABLE 9

Example Natural Frequencies as calculated by Finite Element Analysis of 3-Dimensional CAD files for a 3, 6 and 9 Blade Iron Club Heads of Present Invention.

| 7-Iron | Mode 1 [Hz] | Mode 2 [Hz] | Mode 3 [Hz] |
|---|---|---|---|
| Current Design 1 | 3421 | 4682 | 7403 |
| Prior Art—Traditional Design 1 | 3307 | 4786 | 7401 |
| Current Design 2 | 3463 | 4678 | 7250 |
| Prior Art—Traditional Design 2 | 3449 | 4871 | 7445 |

CONCLUSION

While the invention has been described in detail in terms of specific examples including presently preferred modes of carrying out the invention, those skilled in the art will appreciate that there are numerous variations and permutations of the above described systems and methods. Thus, the spirit and scope of the invention should be construed broadly as set forth in the appended claims.

The invention claimed is:
1. An iron-type golf club head comprising:
a top surface, a sole, a heel, a toe, a hosel and a leading edge;
a ground plane tangent to the sole;
the hosel comprising a hosel bore and a hosel axis;
an origin point at an intersection between the hosel axis and the ground plane;
a ball striking surface having a ball striking area, wherein the ball striking surface defines a heel-side boundary line, a toe-side boundary line, and a ball striking centerline located equidistant between the heel-side boundary line and the toe-side boundary line; and
a rear surface opposite the ball striking surface, the rear surface having a blade portion and a muscle portion with the blade portion separated from the muscle portion by a blade interface, wherein the blade portion and muscle portion laterally extend across the rear surface and further with the blade portion extending from the top surface to the blade interface and with the muscle portion extending from the blade interface to the sole;
wherein the blade interface includes a first blade interface and a second blade interface intersecting the first blade interface at a convergence point located closer to the toe than the heel, wherein the first blade interface extends from the heel to the convergence point and the second blade interface extends from the convergence point to the toe;
a coordinate system centered about the origin point, the coordinate system comprising:
an X axis parallel to the ground plane and parallel to the leading edge;
a Y axis perpendicular to the X axis and oriented away from the rear surface;
a Z axis perpendicular to the ground plane;
wherein the convergence point is located at a position in an X-axis direction from the origin point to the convergence point between 28 to 34 mm;
wherein the muscle portion comprises a toe-side muscle portion height located between the ball striking centerline and the toe-side boundary line and a heel-side muscle portion height located between the ball striking centerline and the heel-side boundary line;

wherein the toe-side muscle portion height and the heel-side muscle portion height are each measured vertically from the sole to the blade interface;

a muscle height toe-heel percentage is a percentage increase of the toe-side muscle portion height over the heel-side muscle portion height; and wherein the muscle height toe-heel percentage is between 110% and 150%.

2. The iron-type golf club head of claim 1, wherein the first blade interface extends parallel to the sole.

3. The iron-type golf club head of claim 1, wherein the second blade interface extends from the convergence point upward toward the toe and top surface.

4. The iron-type golf club head of claim 1, wherein the first blade interface and the second blade interface form an interface angle at the convergence point, and wherein the interface angle is an obtuse angle.

5. The iron-type golf club head of claim 4, wherein the interface angle is between approximately 115 degrees and 155 degrees.

6. The iron-type golf club head of claim 1, wherein the convergence point is closer to the toe-side boundary line than the heel-side boundary line.

7. The iron-type golf club head of claim 1, wherein the blade portion has a generally uniform thickness of between approximately 6 mm and 8 mm, and the muscle portion has a thickness greater than a thickness of the blade portion, wherein a muscle portion thickness is between approximately 8 mm and 16 mm.

8. The iron-type golf club head of claim 1, wherein the rear surface comprises an indentation positioned within the blade portion.

9. The iron-type golf club head of claim 1, wherein the sole has a width between 10 mm and 19 mm measured between the heel-side boundary line and the toe-side boundary line.

10. An iron-type golf club head comprising:
a top surface, a sole, a heel, and a toe;
a ball striking surface having a ball striking area, wherein the ball striking surface defines a heel-side boundary line, a toe-side boundary line, and a ball striking centerline located equidistant between the heel-side boundary line and the toe-side boundary line; and
a rear surface opposite the ball striking surface, the rear surface having a blade portion and a muscle portion with the blade portion separated from the muscle portion by a blade interface, wherein the blade portion and muscle portion laterally extend across the rear surface and further with the blade portion extending from the top surface to the blade interface and with the muscle portion extending from the blade interface to the sole;
wherein the blade interface forms a ledge providing a transition area between the blade portion and the muscle portion;
wherein the muscle portion comprises a toe-side muscle portion height located between the ball striking centerline and the toe-side boundary line and a heel-side muscle portion height located between the ball striking centerline and the heel-side boundary line;
wherein the toe-side muscle portion height and the heel-side muscle portion height are each measured vertically from the sole to the blade interface;

a muscle height toe-heel percentage is a percentage increase of the toe-side muscle portion height over the heel-side muscle portion height; and wherein the muscle height toe-heel percentage is between 110% and 150%.

11. The iron-type golf club head of claim 10, wherein approximately 25% to 35% of a total surface area of the muscle portion is defined on the heel and approximately 65% to 75% of the total surface area of the muscle portion is defined on the toe.

12. The iron-type golf club head of claim 10, wherein the toe-side muscle portion height at the toe-side boundary line is greater than 26 mm and the heel-side muscle portion height at the heel-side boundary line is less than 14 mm.

13. The iron-type golf club head of claim 10, wherein the blade portion has a generally uniform thickness of between approximately 6 mm and 8 mm, and the muscle portion has a thickness greater than a thickness of the blade portion, wherein a muscle portion thickness is between approximately 8 mm and 16 mm.

14. The iron-type golf club head of claim 10, wherein the rear surface comprises an indentation positioned within the blade portion.

15. The iron-type golf club head of claim 10, wherein the sole has a width between 10 mm and 19 mm measured between the heel-side boundary line and the toe-side boundary line.

16. An iron-type golf club head comprising:
a top surface, a sole, a heel, and a toe;
a ball striking surface having a ball striking area, wherein the ball striking surface defines a heel-side boundary line, a toe-side boundary line, and a ball striking centerline located equidistant between the heel-side boundary line and the toe-side boundary line; and
a rear surface opposite the ball striking surface, the rear surface having a blade portion and a muscle portion with the blade portion separated from the muscle portion by a blade interface, wherein the blade portion and muscle portion laterally extend across the rear surface and further with the blade portion extending from the top surface to the blade interface and with the muscle portion extending from the blade interface to the sole;
wherein the muscle portion comprises a toe-side muscle portion height located between the ball striking centerline and the toe-side boundary line and a heel-side muscle portion height located between the ball striking centerline and the heel-side boundary line;
wherein the toe-side muscle portion height and the heel-side muscle portion height are each measured vertically from the sole to the blade interface;
a muscle height toe-heel percentage is a percentage increase of the toe-side muscle portion height over the heel-side muscle portion height; and
wherein the muscle height toe-heel percentage is between 125% and 150%.

17. The iron-type golf club head of claim 16, wherein the toe-side muscle portion height at the toe-side boundary line is greater than 26 mm and the heel-side muscle portion height at the heel-side boundary line is less than 14 mm.

18. The iron-type golf club head of claim 16, wherein the blade portion has a generally uniform thickness of between approximately 6 mm and 8 mm, and the muscle portion has a thickness greater than a thickness of the blade portion, wherein a muscle portion thickness is between approximately 8 mm and 16 mm.

19. The iron-type golf club head of claim 16, wherein the rear surface comprises an indentation positioned within the blade portion.

20. The iron-type golf club head of claim 16, wherein the sole has a width between 10 mm and 19 mm measured between the heel-side boundary line and the toe-side boundary line.

* * * * *